United States Patent
Smith et al.

(10) Patent No.: US 8,376,822 B1
(45) Date of Patent: Feb. 19, 2013

(54) AIR CURTAIN ARRANGEMENT FOR A COLD STORAGE DOORWAY WITH DYNAMIC AIRFLOW-DIRECTING SYSTEM AND METHOD

(76) Inventors: Peter R. Smith, Lewistwon, MT (US); Daniel J. Rhyner, Lewistown, MT (US); Michael E. Pederson, Lewistown, MT (US)

(*) Notice: Subject to any disclaimer, the term of this patent is extended or adjusted under 35 U.S.C. 154(b) by 1469 days.

(21) Appl. No.: 11/823,008

(22) Filed: Jun. 26, 2007

Related U.S. Application Data

(63) Continuation-in-part of application No. 11/649,513, filed on Jan. 4, 2007, now Pat. No. 8,287,337.

(51) Int. Cl.
F24F 9/00 (2006.01)
(52) U.S. Cl. .......................................... 454/188
(58) Field of Classification Search ............... 454/188, 454/189, 190, 191, 192, 193
See application file for complete search history.

(56) References Cited

U.S. PATENT DOCUMENTS

| | | | |
|---|---|---|---|
| 1,090,562 A | 3/1914 | Orr | |
| 1,172,561 A | 2/1916 | Rowntree | |
| 2,283,577 A | 5/1942 | Roby | |
| 2,497,370 A | 2/1950 | Phillips | |
| 2,532,758 A | 12/1950 | Carr | |
| 2,939,374 A | 6/1960 | Caille | |
| 3,018,712 A * | 1/1962 | Wacker | 454/192 |
| 3,190,207 A | 6/1965 | Weisz | |
| 3,215,059 A | 11/1965 | Haas | |
| 3,224,500 A | 12/1965 | Bennett | |
| 3,301,162 A | 1/1967 | Zumbiel | |
| 3,327,935 A | 6/1967 | Berlant | |
| 3,332,334 A | 7/1967 | Melzer | |
| 3,350,994 A | 11/1967 | Guibert | |
| 3,525,483 A | 8/1970 | Van Alstyne | |
| 3,629,973 A | 12/1971 | Bond et al. | |
| 4,008,615 A * | 2/1977 | MacMaster | 374/116 |
| 4,233,938 A | 11/1980 | Ruetenik | |
| 4,516,482 A | 5/1985 | Smith | |
| 4,619,075 A | 10/1986 | Wiles | |
| 4,993,233 A * | 2/1991 | Borton et al. | 62/155 |
| 5,042,198 A | 8/1991 | Privratsky | |
| 5,187,945 A | 2/1993 | Dixon | |
| 5,533,349 A * | 7/1996 | Gromala et al. | 62/129 |
| 6,106,387 A | 8/2000 | Smith | |
| 6,442,957 B1 | 9/2002 | Voogt et al. | |
| 6,470,698 B2 | 10/2002 | Nishi et al. | |
| 6,508,076 B1 | 1/2003 | Gast et al. | |
| 6,595,429 B1 | 7/2003 | Carlson et al. | |
| 6,874,331 B2 | 4/2005 | Chandler et al. | |
| 6,960,129 B2 | 11/2005 | Ashley et al. | |
| 7,475,558 B2 * | 1/2009 | Perry | 62/180 |
| 2004/0134128 A1 | 7/2004 | Berry et al. | |
| 2004/0261318 A1 | 12/2004 | Berry et al. | |
| 2005/0005524 A1 | 1/2005 | Berry et al. | |
| 2007/0039338 A1 * | 2/2007 | Perry | 62/178 |

* cited by examiner

*Primary Examiner* — Steven B McAllister
*Assistant Examiner* — Brittany E Towns
(74) *Attorney, Agent, or Firm* — Shane P. Coleman; Holland & Hart LLP

(57) ABSTRACT

An air curtain arrangement and method of operating the arrangement are provided. The arrangement includes at least one air curtain unit having a supply plenum, a return air duct, and an intermediate air duct therebetween and separates relatively warm and cold areas. The air curtain discharges an air stream across a doorway from an outlet aperture of a discharge plenum toward an air return duct, at a discharge angle. A portion of the air stream is received at an inlet aperture of the return air duct. The portion of the air stream that is received at the air return duct is monitored. The discharge angle is adjusted to maximize the portion of the air that is received. One embodiment controls the discharge angle based on the temperature of the received portion of the air stream. Another embodiment senses the force of the air stream received proximate the inlet aperture.

17 Claims, 20 Drawing Sheets

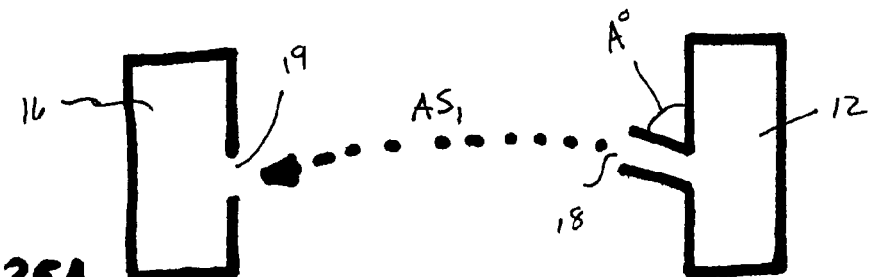
_Fig. 25A_
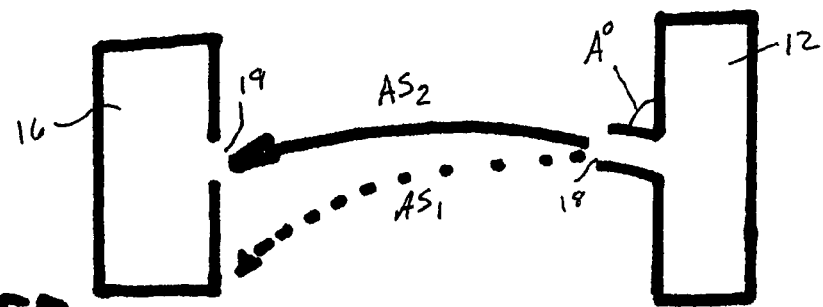
_Fig. 25B_
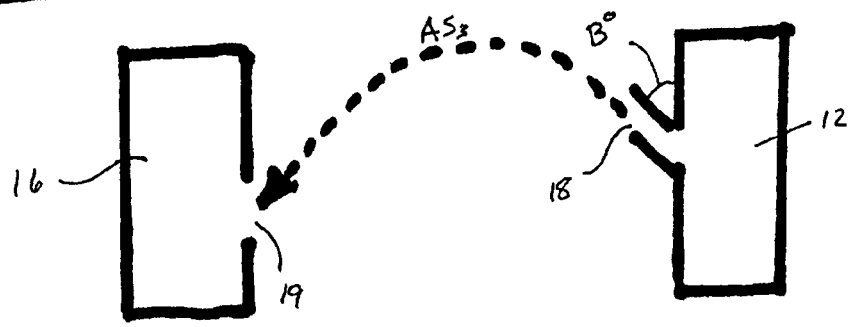
_Fig. 25C_
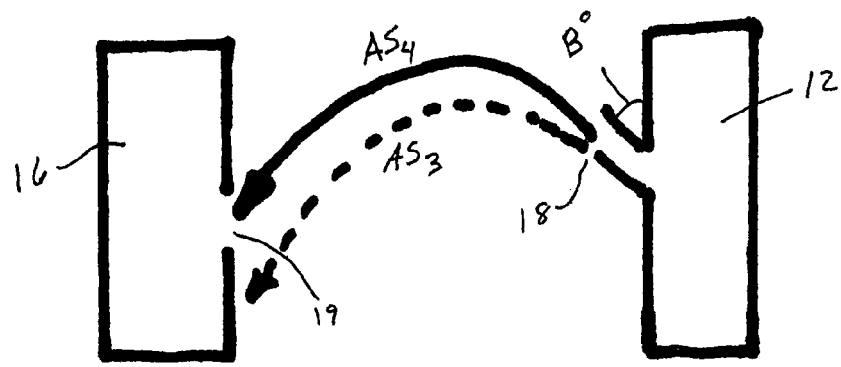
_Fig. 25d_

AIR CURTAIN ARRANGEMENT FOR A COLD STORAGE DOORWAY WITH DYNAMIC AIRFLOW-DIRECTING SYSTEM AND METHOD

RELATED APPLICATIONS

This application is a continuation-in-part of and claims the benefit of a filing date of pending U.S. patent application Ser. No. 11/649,513, filed, Jan. 4, 2007, entitled "Cold Storage Doorway with Airflow Control System and Method," which is hereby incorporated by this reference.

FIELD OF INVENTION

The present invention relates to a conditioned vestibule for a cold storage doorway. More particularly, the present invention relates to an air curtain arrangement and control system that dynamically controls direction and/or velocity of the air discharged across a doorway and a method of controlling the airflow direction and/or velocity.

BACKGROUND INFORMATION

In the field of large cold storage freezers and similar devices, various systems such as solid doors, strip curtains, and air curtains, may be used to separate the cold storage room from an adjacent relatively warm anteroom. It is desirable to allow traffic from people and equipment through a doorway between the cold storage room and the adjacent warm room safely and with a minimum transfer of cool air from the cold room to the warm room.

The use of air curtains is one method of allowing a doorway to remain open to traffic while also preventing substantial energy loss between the cold and warm sides of the doorway. Air curtains generally direct air across the doorway to counter infiltration of warm air from the warm room to the cold room and exfiltration of cold air from the cold room to the warm room. By way of example, air curtains may direct air horizontally across the doorway or vertically, from an upper portion of the air curtain.

As a safety precaution, it is desirable to prevent the formation of fog, ice, and water in the doorway. Ice may form from the mixing of air from the cold and warm sides of the vestibule. The formation of ice at an air curtain depends on the temperature and relative humidity of the cold and warm rooms, and may be characterized by a plot on a psychrometric chart. The mixing of air from the relatively warm and cold sides may be characterized by a straight line between points representing the warm side temperature and humidity and the cold side temperature and humidity, which may be plotted on a psychrometric chart along with the saturation curve. Ice may form whenever the mixing line is to the left of, and above, the psychrometric saturation curve, as it is typically plotted.

The formation of ice may be prevented by heating the air discharged from the air curtain. By way of example, the discharged air may be heated to a temperature at a point on the psychrometric chart such that lines to such point from both the cold side and warm side temperature/humidity points remain to the right of, and below, the psychrometric saturation curve, as it is typically plotted.

While avoiding the formation of ice, water, and fog, it is also desirable to operate the air curtain as efficiently as possible, by adding the minimum amount of heat necessary to avoid such problems. With respect to the psychrometric chart, this means keeping the point representing the airstream with the added heat as close to the saturation curve as possible, without causing mixing lines from this point to the cold side and warm side temperature/humidity points to contact or cross the saturation curve.

Because temperature and humidity conditions in the cold and warm side rooms may change during operation of the air curtain arrangement, it is desirable in some applications to dynamically condition the discharged air in response to changing conditions. Conventional systems have various shortcomings. Some systems permit operation of the air curtain at points directly on the saturation curve. In changing environments, this permits the formation of ice, water, and fog because the system may not respond as quickly as the conditions change and because the sensors may not be sufficiently accurate for all positions in the doorway. This is particularly a problem for systems that rely upon mathematical approximations of the psychrometric saturation curve. Also, conventional control systems do not apply to multiple air curtain arrangements. A transitional vestibule may be formed between two or more air curtains positioned adjacent to each other across a doorway. Multiple air curtain arrangements—particularly those having two or more air curtains—present a more complex situation than do single air curtains. As a result, conventional systems for dynamically conditioning air do not operate efficiently, or even properly, in multiple air curtain arrangements.

Also, conventional air curtain arrangements provide limited ability to change the direction of airflow discharged across the doorway. Direction of the airflow across the doorway affects operation of the air curtain arrangement, and different operating environments may require different discharge angles in order to ensure efficient operation. Typically, airflow direction is fixed during installation and any adjustments made thereafter must be done manually. This is a time-consuming process that is difficult to perform properly by anyone other than a trained technician. Additionally, operating conditions for some air curtain arrangements change throughout the day, so it is impractical to have a trained technician manually adjust airflow operation.

SUMMARY OF THE INVENTION

There exists a need to provide an air curtain and method that more efficiently controls airflow. In one embodiment, an air curtain arrangement is provided, having at least one air curtain unit. The air curtain unit includes a discharge nozzle that discharges an air stream across a doorway that separates a relatively cold side and a relatively warm side. The air curtain unit further includes a return air duct having an inlet aperture that receives at least a portion of the air discharged across the opening. A controller controls a direction of the air stream discharged by the discharge nozzle, based upon (1) a temperature of the air received at the return air plenum, and (2) temperatures on opposing sides of the air curtain unit.

In another embodiment, an air curtain arrangement includes an air discharge means that discharges an air stream across a doorway having a relatively cold side and a relatively warm side, and an air return means that receives a portion of the discharged air and returns the air to the air discharge means. A controller controls direction of the air discharge means to maximize the portion of discharged air that is received at the air return means.

In still another embodiment, an air curtain arrangement for a cold storage doorway is provided. The air curtain arrangement includes a discharge means that discharges an air stream across a doorway having a relatively cold side and a relatively warm side, a heater that warms the air stream, and a first control unit that operates the heater to maintain an air stream temperature. The air curtain arrangement further includes an air return means that receives a portion of the air stream discharged across the opening. A second control unit controls a direction of the discharged air stream to maximize the portion of the discharged air stream that is received by the air return means. An air stream temperature sensor provides an air stream temperature input to the control unit. The first control unit continuously monitors the air stream temperature, and operates the heater to maintain the air stream temperature in a non-saturated state based on a humidity ratio of the air stream.

In still another embodiment, an air curtain arrangement is provided for a cold storage doorway. The air curtain arrangement includes means for directing an air stream across the doorway having a relatively warm side and a relatively cold side, means for receiving at least a portion of the air stream, means for maintaining a temperature at the air stream based on a humidity ratio associated with the doorway, and means for controlling a discharge direction of the air stream in order to maximize the portion of the air stream that is received.

In still another embodiment, a method of operating an air curtain arrangement is provided. According to the method, an air stream is discharged across a doorway. A portion of the air stream is received at an inlet aperture of a return duct. A temperature of the received portion of the air stream and temperatures on opposing sides of the air curtain arrangement are sensed. The air stream is discharged at a discharge direction that is based upon the temperature of the received portion of the air stream and the temperatures on the opposing sides of the air curtain arrangement.

In still another embodiment, a method is provided for controlling air stream temperature of an air curtain used in connection with an air curtain arrangement for a cold storage doorway that separates relatively warm and cold sides. According to the method, warm and cold side temperatures are continuously monitored. An air stream temperature is continuously determined, based upon the warm and cold side temperatures and a humidity ratio of the air stream. The air stream temperature is sufficient to operate in a non-saturated state. The air stream is directed across the doorway at a direction based upon the warm and cold side temperatures and a temperature of a portion of the air stream that is received across the doorway at a return air duct. The air stream is maintained at the air stream temperature.

In still another embodiment, a method is provided for maintaining an air stream temperature of an air curtain in a doorway between a relatively cold side and a relatively warm side. According to the method, temperatures of a relatively warm and a relatively cold side of a doorway are continuously monitored. The doorway includes an air curtain arrangement that directs an air stream across the doorway. The air stream is maintained at a temperature based on the temperatures of the relatively warm side and the relatively cold side, and based on a humidity ratio of mixed air in the air curtain arrangement. The air stream is directed across the doorway at an angle based upon a comparison of the temperatures of the relatively warm side and the relatively cold side with a temperature of a portion of the air stream that is received across the doorway by a return air duct.

In still another embodiment, a control unit is provided for controlling the temperature of an air stream directed across a doorway by one or more air curtains that are part of an air curtain arrangement positioned across the doorway separating relatively warm and cold air masses. The control unit includes a processor and a storage arrangement. The storage arrangement stores computer-executable instructions for execution by the processor to control operation of the air curtain arrangement. The instructions include instructions for continuously monitoring a portion of the air stream that is received by an air return duct, and adjusting a direction of discharge of the air stream to maximize the portion of the air stream that is received by the air return duct.

In still another embodiment, an apparatus is provided for forming an air stream across a doorway between areas of relatively cool and warm air masses. The apparatus includes a supply air plenum with an outlet aperture at a first side of the doorway, a return air duct with an inlet aperture at a second side of the doorway and an intermediate air duct extending between the supply plenum and return air duct. An air mover moves an air stream across the doorway into the inlet aperture to the return air duct through the intermediate air duct to the supply air plenum and out of the outlet aperture at a discharge direction that maximizes a portion of the air stream that is received at the inlet aperture. A heater is in thermal communication with the air stream for warming the air stream. At least one control unit controls the operation of the heater and the discharge direction of the air stream. A first air sensor is located in one of the relatively cool and warm air areas and provides an air characteristic input to the control unit. A second air sensor is located in contact with the air stream and provides an air stream characteristic input to the control unit. The control unit continuously monitors the air characteristic input and the air stream characteristic input and operates the heater to maintain operation of the apparatus in a non-saturated state and adjusts the discharge direction to maximize the portion of the air stream that is received at the inlet aperture.

In still another embodiment, an apparatus is provided for forming at least two air streams across a doorway between areas of relatively cool and warm air masses using first and second air curtains. Each air curtain includes a supply air plenum with an outlet aperture at one side of the doorway, a return air duct with an inlet aperture at another second of the doorway and an intermediate air duct extending between the supply plenum and return air duct, and an air mover for moving an air stream across the doorway into the air curtain's respective inlet aperture to the return air duct through the intermediate air duct to the supply air plenum and out of the outlet aperture. A heater is in thermal communication with the air stream from at least one of the air curtains and warms the air stream of the particular air curtain. A control unit controls the operation of the heater. A first air sensor is located in one of the relatively cool and warm air areas and provides an air characteristic input to the control unit. A second air sensor is located in contact with the air stream and provides an air stream characteristic input to the control unit. The control unit continuously monitors the air characteristic input and the air stream characteristic input, and operates the heater to maintain a non-saturated state, and adjusts a discharge direction of the air stream to maximize a portion of the air stream that is received at the inlet aperture.

In still another embodiment, a method is provided for operating an air curtain arrangement that separates a relatively warm area from a relatively cold area. According to the method, an air stream is discharged across a doorway from an outlet aperture of a discharge plenum toward an air return duct at a discharge angle. A portion of the air stream is received at an inlet aperture of the return air duct. The portion of the air stream that is received at the air return duct is monitored. The discharge angle is adjusted to maximize the portion of the air that is received.

BRIEF DESCRIPTION OF DRAWINGS

The detailed description will refer to the following drawings, wherein like numerals refer to like elements, and wherein:

FIGS. 25A-25D show an embodiment in which the discharge nozzle may be positioned at one of two discrete positions, angles A°, B°.

DETAILED DESCRIPTION

Figure 1:
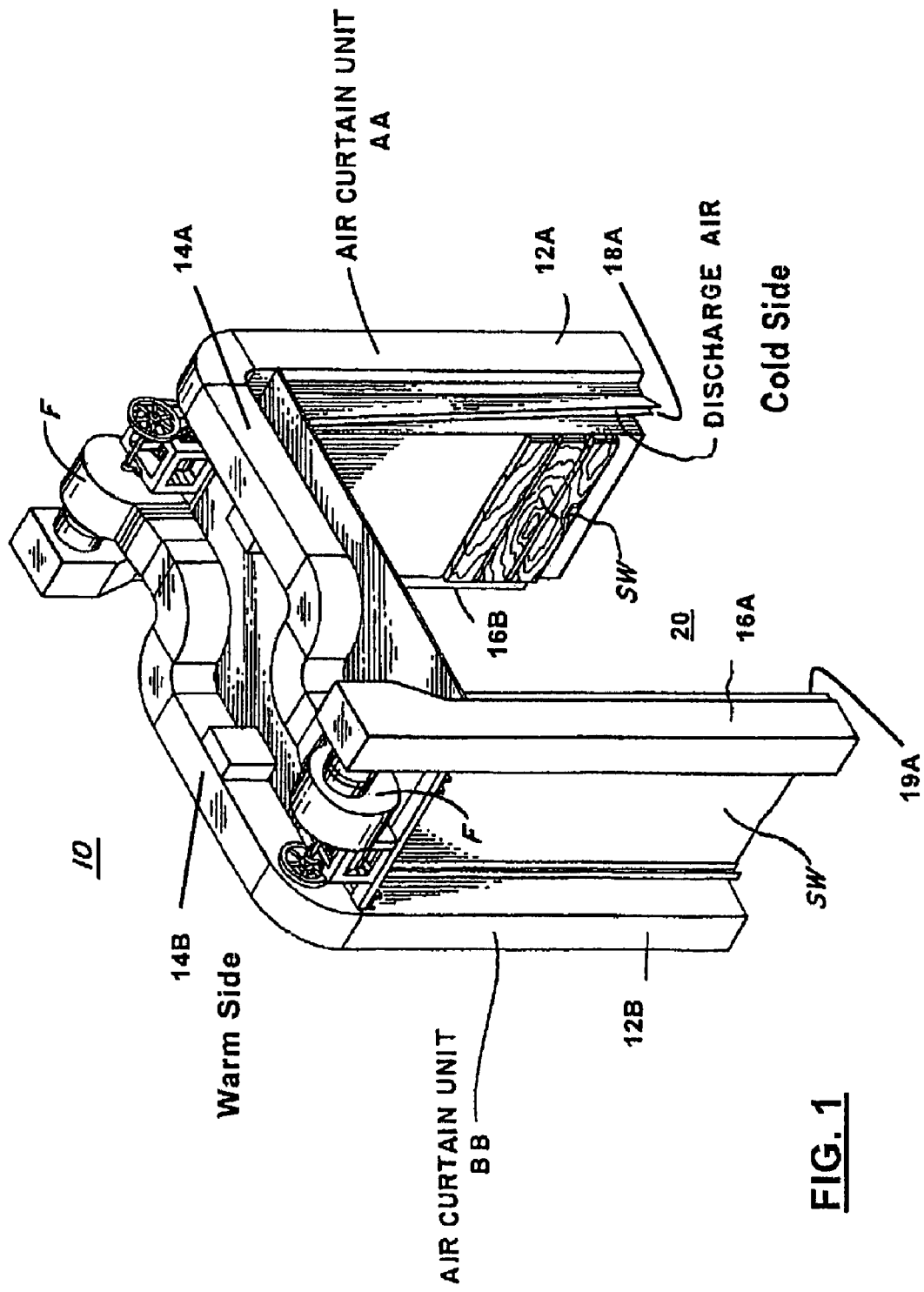
FIG. 1 shows a perspective view of one embodiment of an air curtain arrangement comprising two horizontal air curtains.

FIG. 1 shows a perspective view of one embodiment of an air curtain arrangement 10 according to the present invention. Embodiments of an air curtain arrangement may include one or more air curtain units (e.g., AA, BB in FIG. 1). As used herein, an air curtain unit (or air curtain) refers to an apparatus having at least a supply air plenum 12A, 12B with an outlet aperture (also referred to sometimes as a "discharge nozzle") 18A that discharges air across the doorway 20, a return air duct 16A, 16B with an inlet aperture 19A that receives the air discharged across the doorway 20, and an intermediate air duct 14A, 14B extending between the supply plenum 12A, 12B and return air duct 16A, 16B, or equivalent components. Air curtains may direct air across the doorway 20 horizontally, vertically, or otherwise. Air curtain arrangements having two or more air curtains are sometimes referred to as "vestibules." Vestibules having multiple air curtains may use different types of air curtains or air curtains in different configurations, or both. For example, a vestibule may include first and second horizontal air curtains that direct air in opposite directions across the doorway.

The embodiment of FIG. 1 includes first and second air curtain units AA, BB that each direct air horizontally across the doorway 20 in opposite directions. In this embodiment, the air curtain units AA, BB are separated by side walls SW. The air curtain arrangement 10 of FIG. 1 includes a control unit (not shown) that controls temperature of the air discharged across the doorway 20 by at least one of the air curtains AA, BB. In the embodiment shown in FIG. 1, an air mover, such as the fan F, directs air through the air curtains AA, BB. A heater (not shown) warms the air in the first air curtain AA (nearest the relatively cold side) to a temperature controlled by the control unit. In one embodiment, the heater (not shown) may be located in the intermediate air duct 14A, 14B near the fan F. In one embodiment, the heater heats the air only in the air curtain unit AA nearest the freezer. The control unit specifies a temperature for the heater that ensures that the vestibule operates below the psychrometric saturation curve to ensure that frost, ice, and fog do not form in the doorway 20. The control unit is electrically connected to the heater and may be positioned in any convenient location.

Figure 2:
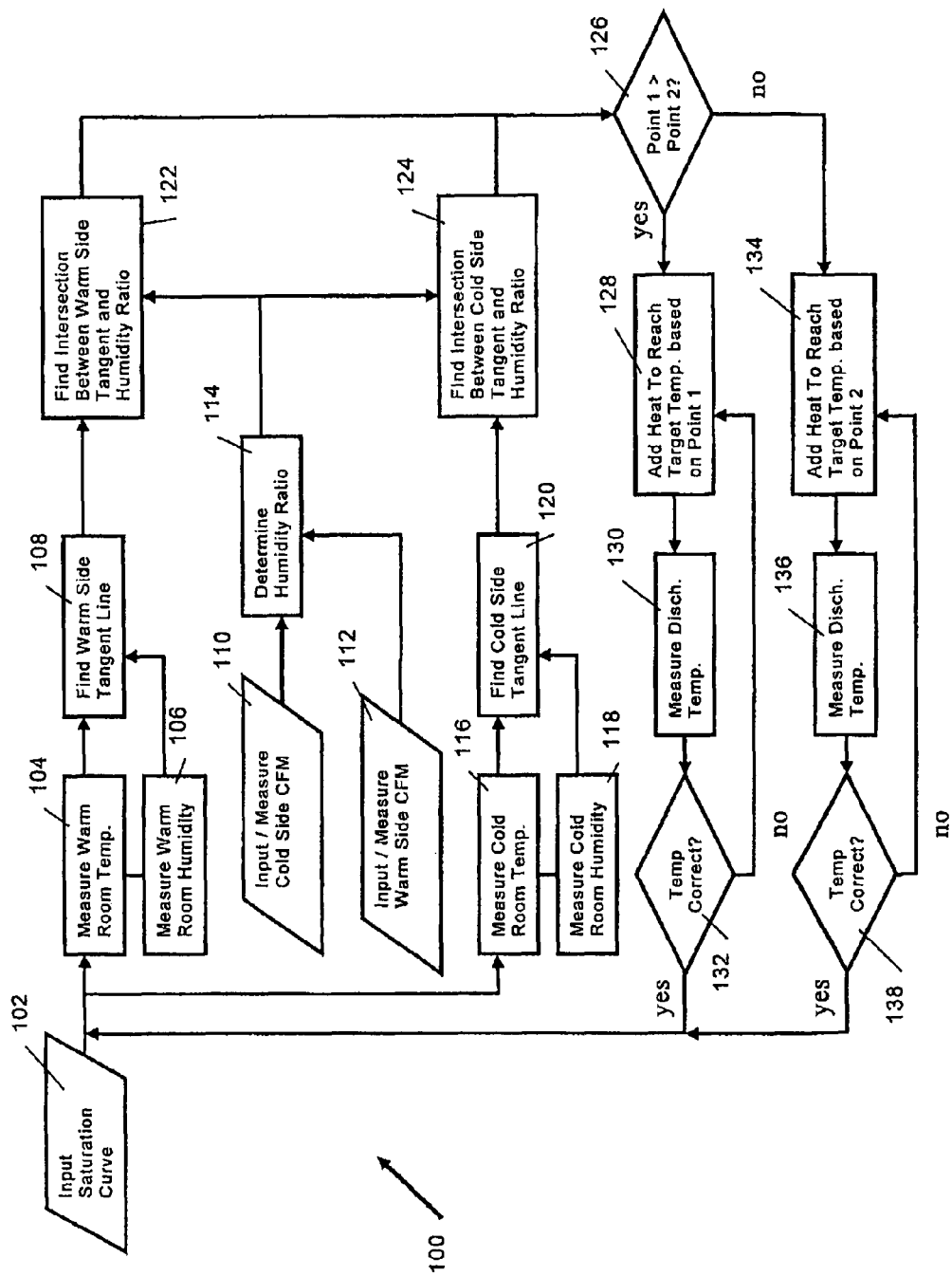
FIG. 2 shows a flowchart of one embodiment of the method of controlling temperature of an air stream discharged by an air curtain in a multiple air curtain vestibule.
Figure 3:
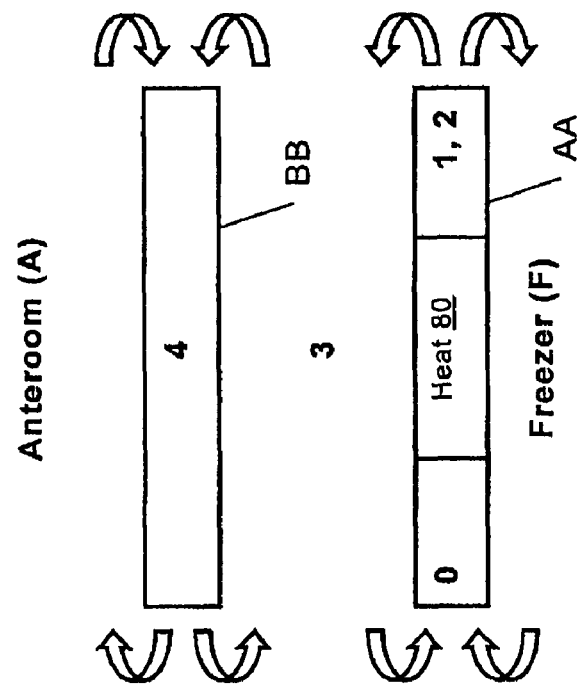
FIG. 3 shows a schematic view of the air curtain arrangement of FIG. 1.

FIG. 2 shows a flowchart of one embodiment of the method 100 of controlling temperature of an air stream discharged by an air curtain (e.g., AA, BB in FIG. 1) in a multiple air curtain arrangement 10. By way of example, the method 100 of FIG. 2 may be applied to an arrangement 10 having two air curtains AA, BB such as shown in FIG. 1. FIG. 3 shows a schematic view of the air curtain arrangement 10 of FIG. 1, for reference of the method 100 of FIG. 2. The exemplary embodiment of FIG. 3 includes two air curtains AA, BB across the doorway 20. The first air curtain AA is near the freezer F (i.e., the relatively cold side), and the second air curtain BB is near the anteroom A (i.e., the relatively warm side). Point 0 represents conditions (e.g., temperature and humidity) of the return air to the first air curtain AA. The first air curtain AA heats the returning air and discharges the air across the doorway 20. The first air curtain AA heats the air to a discharge temperature sufficient to prevent the formation of ice in the doorway 20. Points 1 and 2 represent different possible conditions of the discharge air, one of which points is selected by the method and system described herein. Point 3 represents a condition of air at a point between the first and second air curtains AA, BB. Point 4 represents a condition of air circulating in the second air curtain BB. In this embodiment, the second air curtain BB does not heat the air.

In the example method 100 of FIG. 2, a psychrometric saturation curve (also referred to as the saturation curve) is input 102 to a control unit. Saturation curves vary depending upon barometric pressure, so the saturation curve that is appropriate to the conditions in which the air curtain arrangement 10 operates is selected. In another embodiment, the barometric pressure may be calculated by a control unit using a pressure sensor input, and the control unit may calculate the saturation curve or select the curve from multiple curves representing different barometric pressures, which may be stored as data in memory of the control unit or external memory, for example.

One or more air characteristics are input to the control unit from the warm side A. In the embodiment shown in FIG. 2, the warm side temperature is measured 104, and the warm side humidity is measured 106, using sensors on the warm side A. The warm side temperature and humidity are input to the control unit. Based on the warm side temperature and humidity (e.g., illustrated as a point on the psychrometric chart in FIGS. 4 and 5), the control unit calculates 108 a warm side tangent line to the psychrometric saturation curve.

Figure 4:
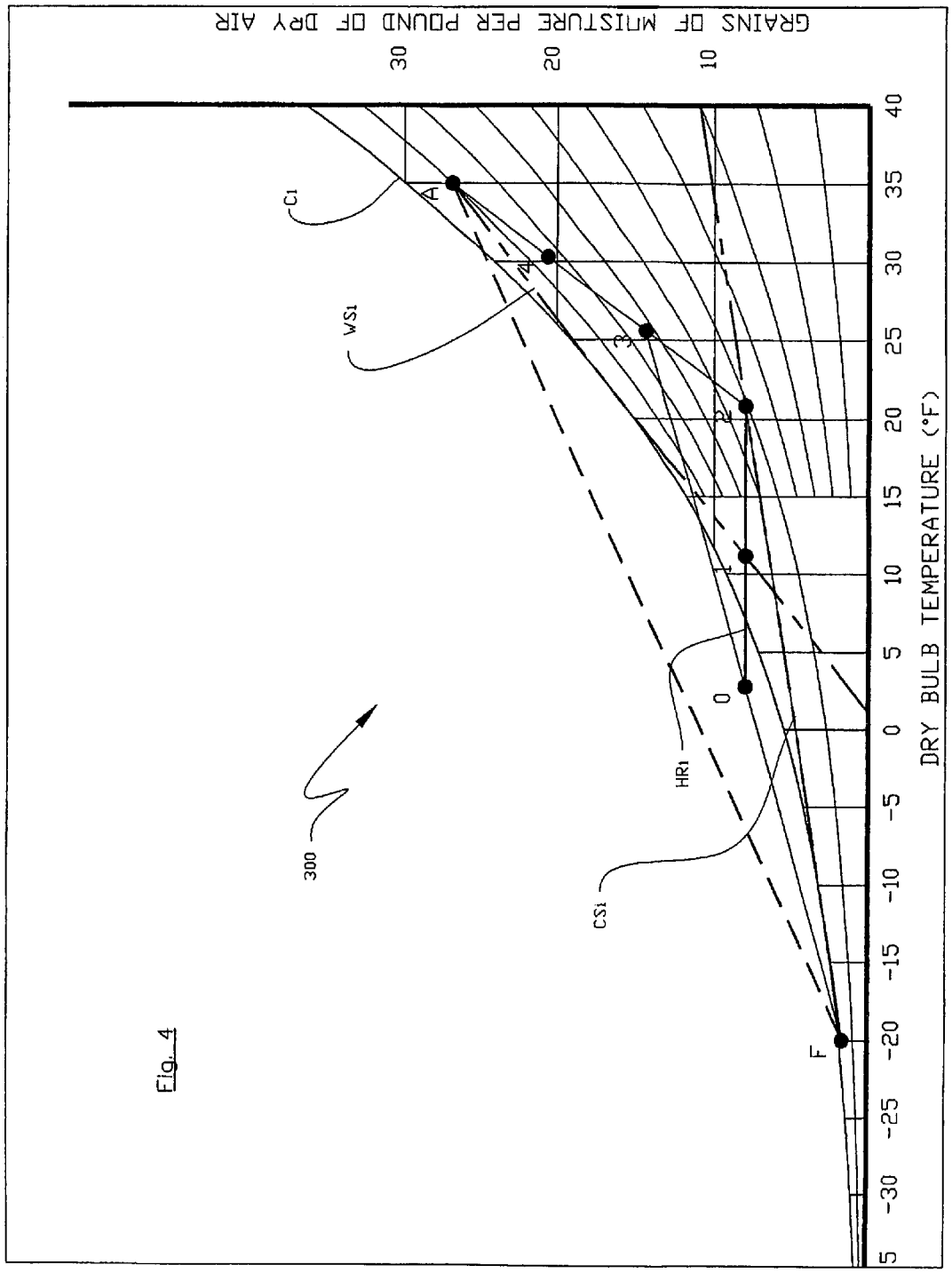
FIG. 4 shows psychrometric saturation curves with example data to illustrate the operation of the method of FIG. 2.
Figure 5:
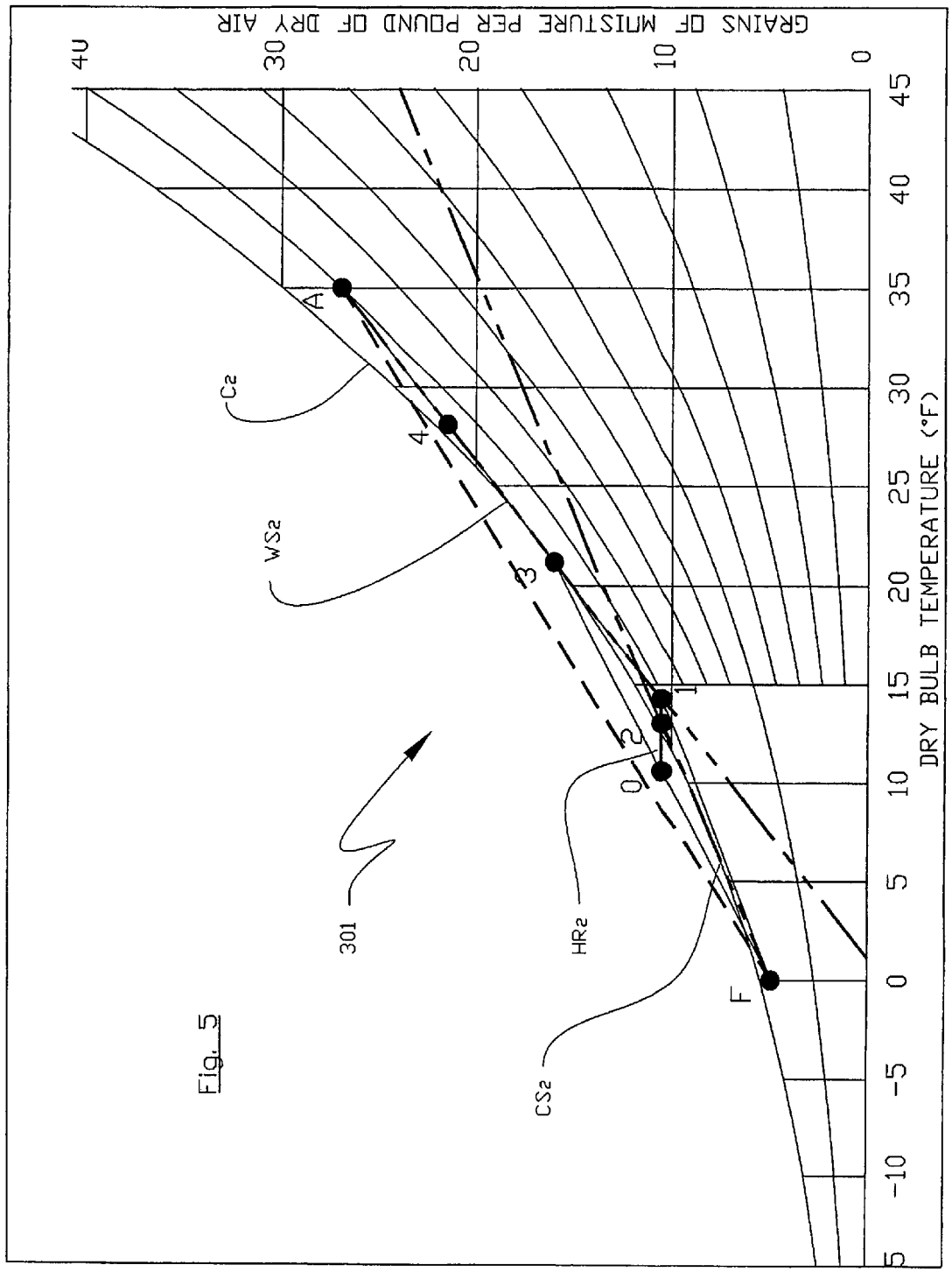
FIG. 5 shows psychrometric saturation curves with another example data to illustrate the operation of the method of FIG. 2.

FIGS. 4 and 5 show psychrometric charts 300, 301 with example data to illustrate the operation of the method 100 of FIG. 2. Curves $C_1$, $C_2$ are illustrated in a manner that is commonly used in the art and are the actual psychrometric saturation curves. In FIGS. 4 and 5, the points A and F represent the humidity and temperature of the relatively warm and cold sides (e.g., points A and F in FIG. 3), as plotted on the psychrometric chart. The warm side conditions (point A) are the same for both FIGS. 4 and 5, but the cold side room is warmer in the example of FIG. 5 than it is in FIG. 4 (0 degrees Fahrenheit in FIG. 5 versus −20 degrees Fahrenheit in FIG. 4). In both FIGS. 4 and 5, the dashed lines $WS_1$, $WS_2$ passing through point A and point 1, which is tangent to the saturation curves $C_1$, $C_2$, represent the warm side tangent lines calculated at block 108 in FIG. 2. The lines $CS_1$, $CS_2$ represent the cold side tangent lines.

The cold side tangent lines $CS_1$, $CS_2$ pass through point F and Point 2, and are also tangent to the respective curves $C_1$, $C_2$. The dashed lines from point F to point A represent the mixing line of air between the relatively cold and warm sides (e.g., air moving between point A and point F on the schematic of FIG. 3) in the absence of heat added by at least one of the air curtains AA, BB in the air curtain arrangement 10. In both examples, the A-F mixing lines lie above the saturation curves $C_1$, $C_2$, which means that ice, water, or fog could form in the doorway 20 without the addition of heat.

Referring to FIG. 2, the airflow from the warm side air curtain BB is input 112 to the control unit, and the airflow from the cold side air curtain AA is input 110 to the control unit. In the embodiment shown, the airflow is input as a volumetric airflow value in cubic feet per minute (CFM). In one embodiment, the airflow is input to the control unit manually, as a fixed value for the air curtain arrangement 10. The related examples shown in FIGS. 4 and 5 illustrate an embodiment having two air curtains AA, BB each having the same airflow (e.g., each having the same-sized, fixed-speed fans). In a two-curtain arrangement in which each air curtain AA, BB has the same, fixed airflow, the humidity ratio HR, line is illustrated on the psychrometric chart as a horizontal line one-quarter of the way between points F and A, as shown in FIGS. 4 and 5. The fixed airflow volume for each air curtain AA, BB is input 110, 112 (for example, into a control unit (50 in FIG. 6) that performs the method 100) as fixed values for each air curtain AA, BB. In other embodiments, the airflow may be different for each air curtain AA, BB and/or may change during operation. Sensors (not shown) may be used to monitor the actual airflow and may provide airflow input data to the control unit (50 in FIG. 6). The control unit (50 in FIG. 6) defines 114 horizontal humidity ratio line $HR_1$, $HR_2$ based on the airflow across the air curtain arrangement 10, which can be adjusted based upon the size of fans in the air curtain AA. These humidity ratio lines $HR_1$, $HR_2$ are shown in FIGS. 4 and 5 as horizontal lines at point 0 and passing through points 1 and 2. Stated differently, point 1 is defined as the intersection on the psychrometric saturation chart of the warm side tangent line $WS_1$, $WS_2$ and the humidity ratio line $HR_1$, $HR_2$. Point 2 is defined as the intersection of the cold side tangent line $CS_1$, $CS_2$ and the humidity ratio line $HR_1$, $HR_2$.

Air characteristics of the cold room F are also measured and input to the control unit. In the embodiment of FIG. 2, the air characteristics of temperature and humidity are measured. The cold room temperature is measured 116 and input to the control unit. The cold room humidity is measured 118 and input to the control unit. Based on the cold room temperature and humidity, the control unit determines 120 a cold side tangent line $CS_1$, $CS_2$ to the saturation curve $C_1$, $C_2$. In the example plots of FIGS. 4 and 5, these cold side tangent lines $CS_1$, $CS_2$ are represented by lines from point F through point 2, which is tangent to the curve $C_1$, $C_2$.

First and second temperatures are calculated based on the cold side and warm side tangent lines $CS_1$, $CS_2$, $WS_1$, $WS_2$. A first temperature is determined 122 by the intersection point between the warm side tangent line $WS_1$, $WS_2$ and the humidity ratio line $HR_1$, $HR_2$, which is shown as point 1 in FIGS. 4 and 5. A second temperature is determined 124 by the intersection point between the cold side tangent line $CS_1$, $CS_2$ and the humidity ratio line $HR_1$, $HR_2$, which is shown as point 2 in FIGS. 4 and 5.

The control unit uses the larger of the first and second temperatures to determine how much heat to add to the air curtain AA. The selected temperature (point 1 or 2) is the air discharge temperature of the air curtain AA, shown by points 1 and 2 on the schematic of FIG. 3. In the example method 100 of FIG. 2, the control unit determines 126 whether the first or second temperature is greater. If the first temperature is greater ("yes" branch at block 126), then the control unit causes the heater to add heat 128 based on the first temperature. In this embodiment, heat is added at a preset increment. The air discharge temperature is measured 130. The control unit determines 132 whether the air stream temperature has reached a target temperature based on the first temperature. If the target temperature is not yet reached ("no" branch at block 132), the control unit continues to add heat 128 until the target temperature is reached. Once the target temperature is reached ("yes" branch at block 132), the method 100 returns to the steps of measuring the warm side and cold side temperature and humidity (blocks 104, 106, 116, 118). In one embodiment, the control unit causes the heater 80 to add heat until the air stream temperature exceeds the first temperature by a predetermined amount (e.g., 10 degrees greater than the first temperature). If the second temperature is greater ("no" branch at block 126), then the control unit causes the heater to add heat 134, and the air discharge temperature is measured 136. The control unit determines 138 whether the air discharge temperature has reached a target temperature based on the second temperature. If the target temperature is not yet reached ("no" branch at block 138), the control unit causes the heater 80 to continue to add heat 134 until the target temperature is reached. Once the target temperature is reached ("yes" branch at block 138), the method 100 returns to the steps of measuring the warm side and cold side temperature and humidity (blocks 104, 106, 116, 118).

As described with respect to blocks 126, 128, 130, 132, 134, 136, 138, the control unit warms the air stream to a target temperature based on the greater of the first and second temperatures. The target temperature is at least as great as the greater of the first and second temperatures. In one embodiment, the target temperatures are greater than the first and second temperatures by a margin factor (e.g., 10 degrees Fahrenheit). This margin factor ensures that the mixing lines remain below the saturation curves (e.g., $C_1$, $C_2$), and that frost, ice, and fog does not form in the doorway 20. In the example of FIG. 4, the second temperature, represented by the intersection of the cold side tangent line $CS_1$ and the humidity ratio line HR, (point 2), is greater than the first temperature, so the control unit causes the heater to warm the discharge air stream to a temperature that is at least as great as the second temperature. In the example of FIG. 5, the first temperature, represented by the intersection of the warm side tangent line $WS_2$ and the humidity ratio line $HR_2$ (point 1), is greater than the second temperature, so the control unit warms the discharge air stream to a temperature that is at least as great as the first temperature.

Figure 6:
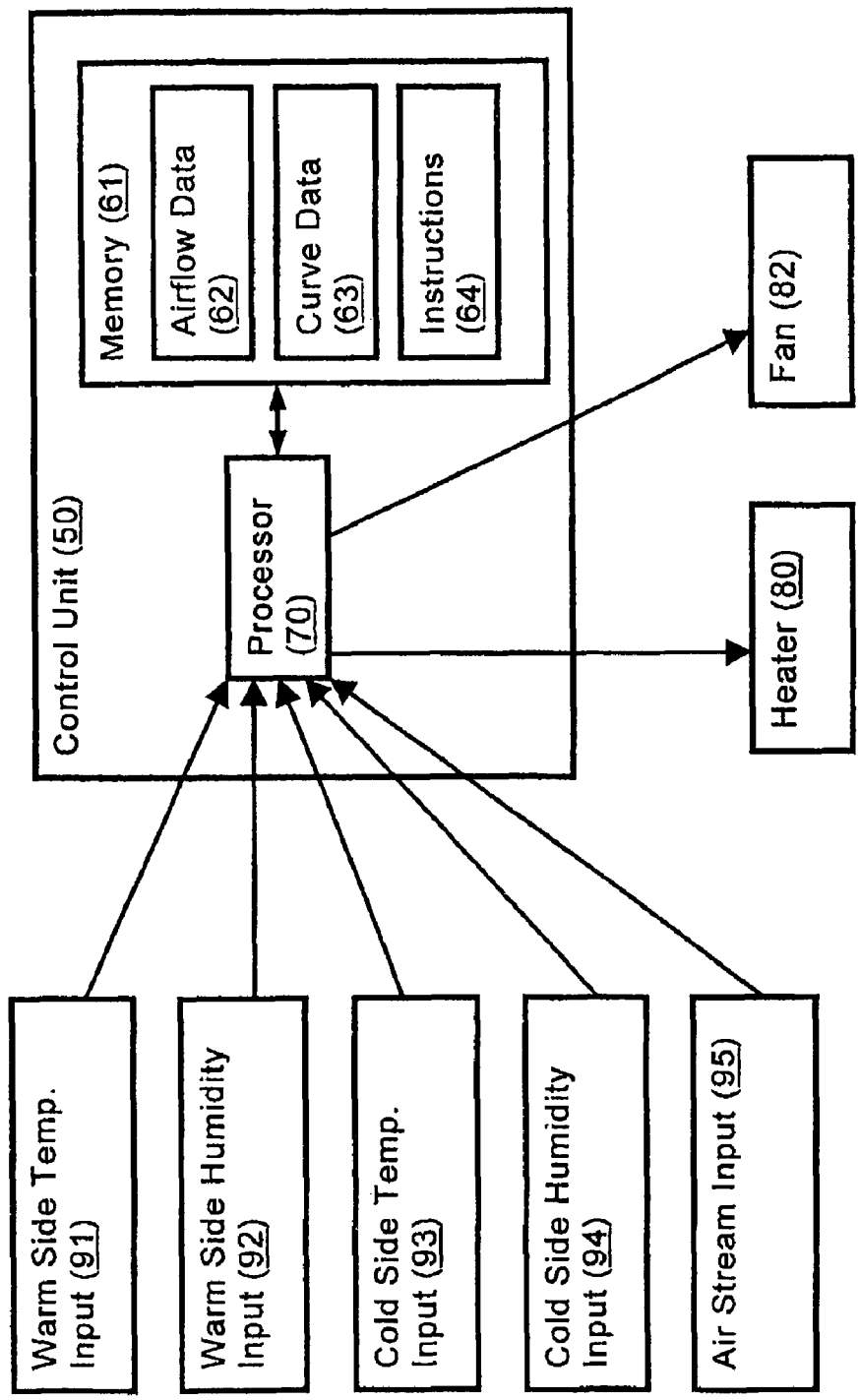
FIG. 6 shows a block diagram of a control unit that may be used to implement the method described with respect to FIG. 2.

FIG. 6 shows a block diagram of a control unit 50 that may be used to implement the method 100 described with respect to FIG. 2. The control unit 50 includes a processor 70 and a memory 61. In this embodiment, a storage arrangement such as memory 61 stores instructions 64 to be executed by the processor 70 to perform the functions to control temperature of airflow in the air curtain arrangement 10, such as the functions specified in the method 100 described with respect to FIG. 2. In the embodiment shown, the processor 70 receives air characteristic inputs 91-94 from one or more air characteristic sensors described herein, including a warm side temperature input 91, a warm side humidity input 92, a cold side temperature input 93, and a cold side humidity input 94. Data input from the sensors may be stored, for example, in the memory 61. The memory 61 may also store values such as the saturation curve data 63 and the airflow data 62 described in the example of FIG. 2. Based upon the air characteristic inputs 91-94, the instructions cause the processor 70 to send a signal to the heater 80 of the air curtain AA to control temperature of the airflow in the air curtain arrangement 10. In addition, the processor 70 receives an air stream input 95 from an air stream sensor, such as a temperature sensor, that measures the air stream. In one embodiment, the heater 80 is positioned in the air curtain (e.g., AA in FIG. 1) nearest the freezer F. The control unit 50 continuously monitors the air stream input 95 to adjust the air stream temperature in real time to maintain the air curtain arrangement 10 in a non-saturated condition. The controller 70 may also control one or more fans 82 in one or more of the air curtains AA, BB as described further with respect to FIG. 10.

Figure 7:
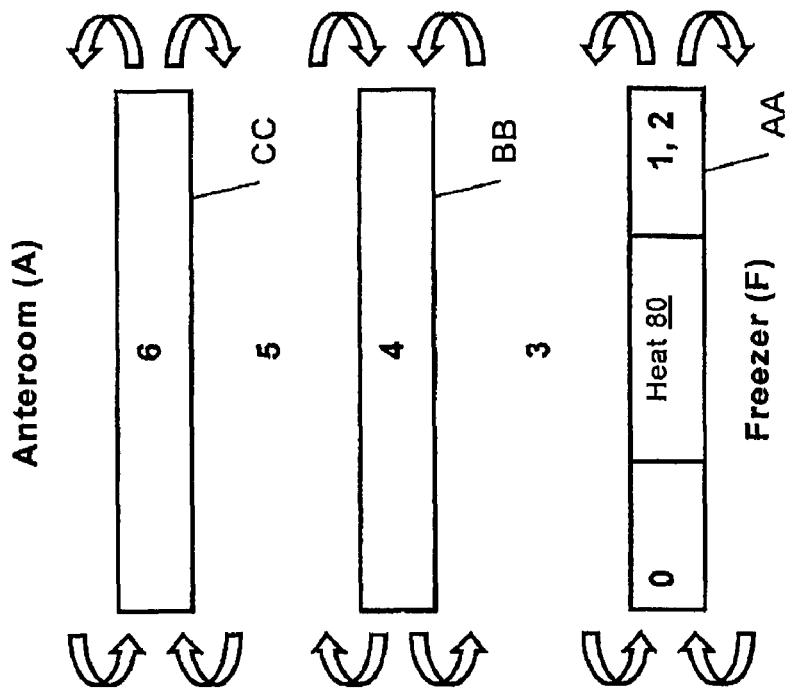
FIG. 7 shows a schematic of an exemplary triple air curtain arrangement between a freezer and an anteroom, having a heater in the first air curtain.

The present invention may be extended beyond double air curtain embodiments to include embodiments having multiple air curtains. FIG. 7 shows a schematic of an exemplary triple air curtain arrangement between a freezer F and an anteroom A, having a heater 80 in the first air curtain AA. Point 0 represents conditions at a point at an intake (e.g., 19A in FIG. 1) of the first air curtain AA. Points 1 and 2 represent conditions at a point at a discharge (e.g., 18A in FIG. 1) of the first air curtain AA. Point 3 represents conditions at a point between the first and second air curtains AA, BB. Point 4 represents conditions at a point within the second air curtain BB. Point 5 represents conditions at a point between the second and third air curtains BB, CC. Point 6 represents conditions at a point within the third air curtain CC.

Figure 8:
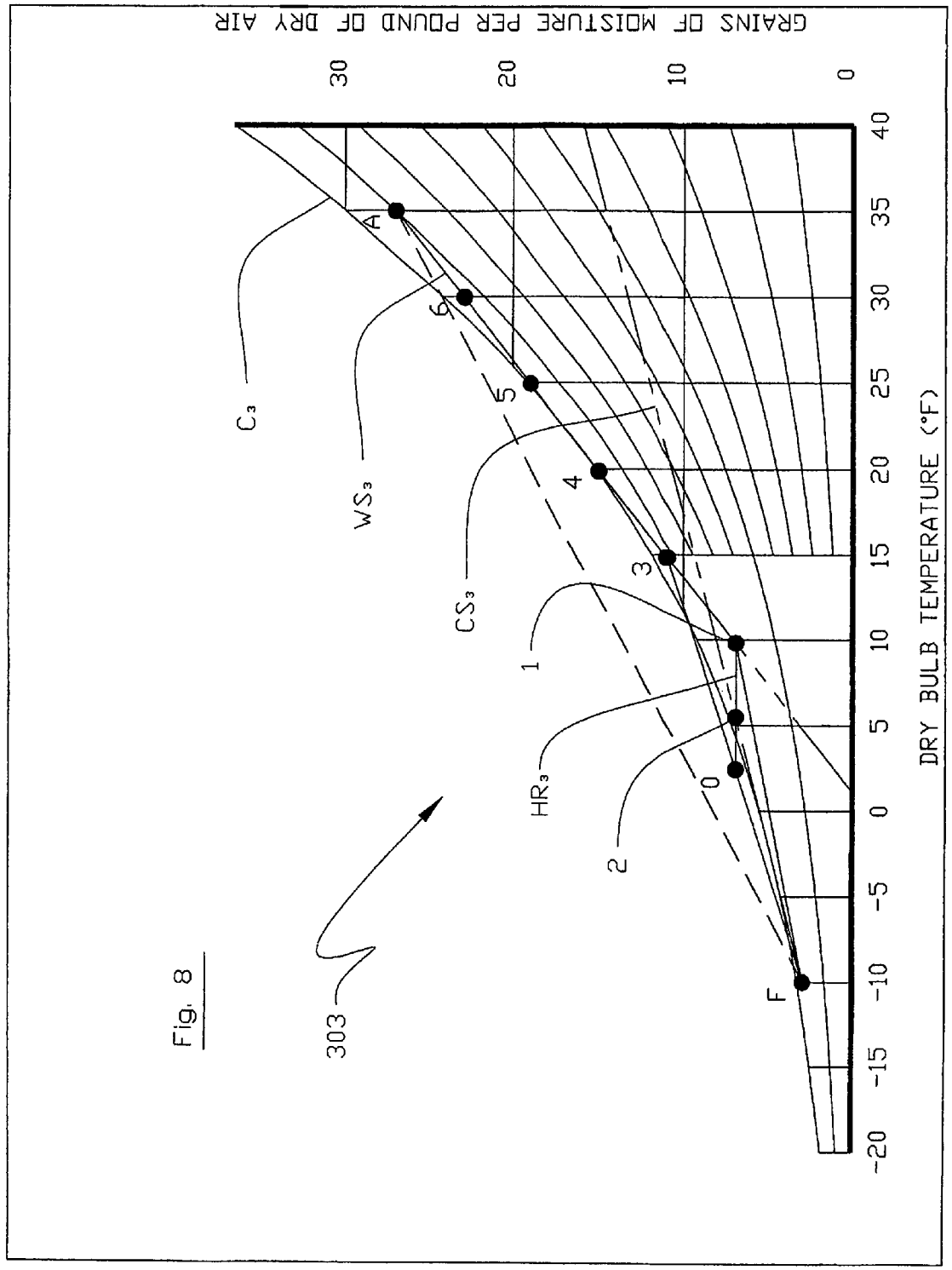
FIG. 8 shows an example psychrometric chart for a triple air curtain arrangement.
Figure 9:
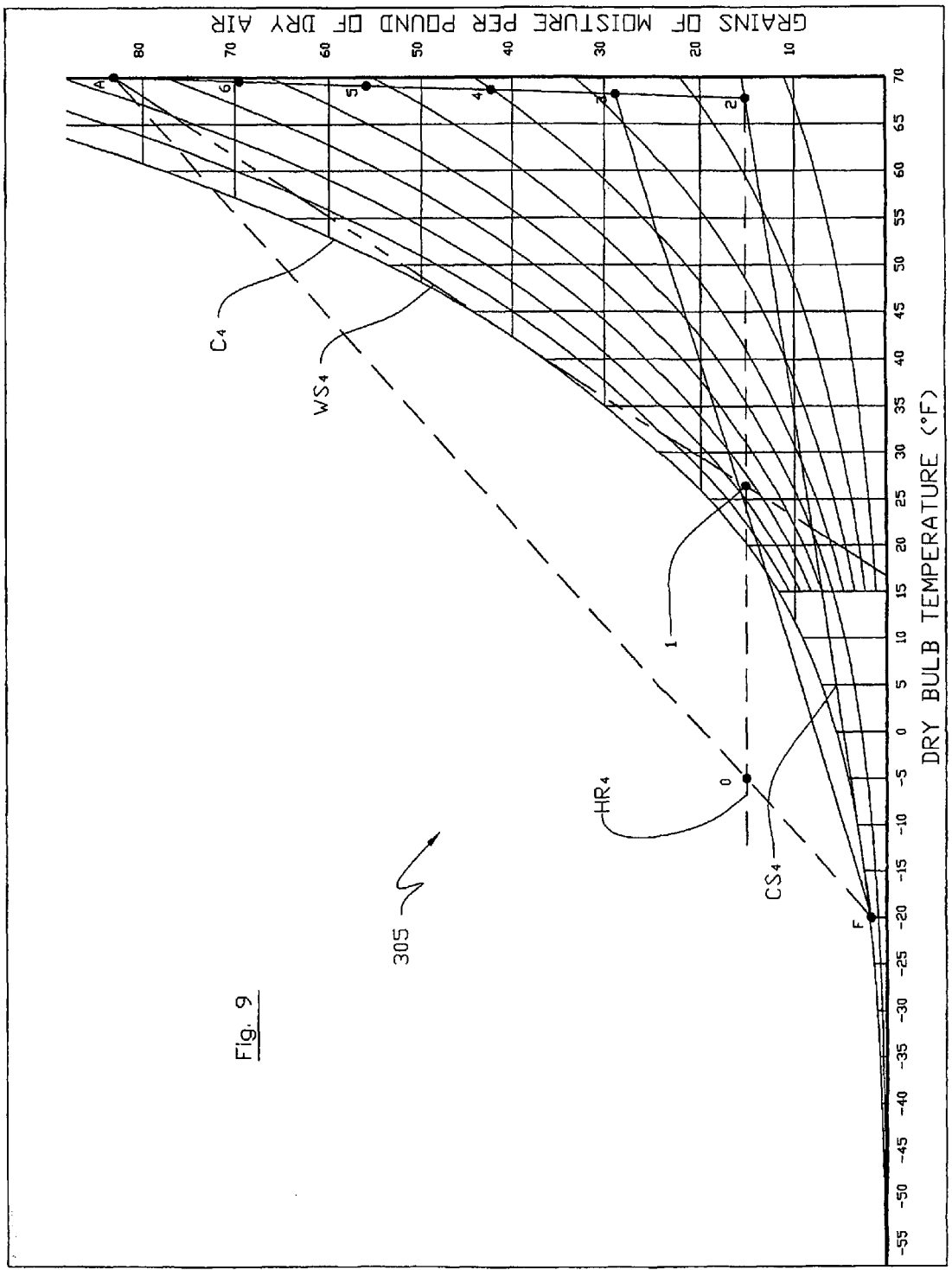
FIG. 9 shows an another example psychrometric chart for a triple air curtain arrangement.

FIGS. 8 and 9 show example psychrometric charts 303, 305 for a triple air curtain arrangement. Points 0-6 in FIG. 7 correspond to points 0-6 on the saturation curves of FIGS. 8 and 9. FIG. 8 reflects an example in which the freezer is maintained at −10 degrees Fahrenheit, and the anteroom is 35 degrees Fahrenheit.

In the example of FIG. 8, the warm side tangent line $WS_3$ is illustrated as the dashed line passing through point A, tangent to the curve $C_3$. The cold side tangent line $CS_3$ is illustrated as the dashed line passing through point F, tangent to the saturation curve $C_3$. The humidity ratio in this example is determined based upon the relative airflow of the air curtains AA, BB, CC, and is represented by the horizontal humidity ratio line $HR_3$ passing through point 0. Point 1 represents the intersection of the humidity ratio line $HR_3$ and the warm side tangent line $WS_3$. Point 2 represents the intersection of the humidity ratio line $HR_3$ and the cold side tangent line $CS_3$. In applying the method 100 of FIG. 2 to this example, point 1 (approximately 10 degrees Fahrenheit) is used to determine the target temperature, because point 1 is greater than point 2. Heat is added to the air curtain arrangement 10 (e.g., at the first air curtain AA) based upon this target temperature.

FIG. 9 reflects an example psychrometric chart 305 for which point 2 is greater than point 1, due to the operating conditions of the air curtain arrangement 10. In the example of FIG. 9, the warm side tangent line $WS_4$ is illustrated as the dashed line passing through point A, tangent to the saturation curve $C_4$. The cold side tangent line $CS_4$ is illustrated as the line passing through point F, tangent to the saturation curve $C_4$. As with the example of FIG. 8, the humidity ratio in this example is determined based upon the relative airflow of the air curtains AA, BB, CC, and is represented by the horizontal humidity ratio line $HR_4$ passing through point 0. Point 1 represents the intersection of the humidity ratio line $HR_4$ and the warm side tangent line $WS_4$. Point 2 represents the intersection of the humidity ratio line $HR_4$ and the cold side tangent line $CS_4$. In applying the method 100 of FIG. 2 to this example, point 2 (approximately 68 degrees Fahrenheit) is used to determine the target temperature, because point 2 is greater than point 1 in this example. Heat is added to the air curtain arrangement (e.g., at the first air curtain AA) based upon this target temperature.

Figure 10:
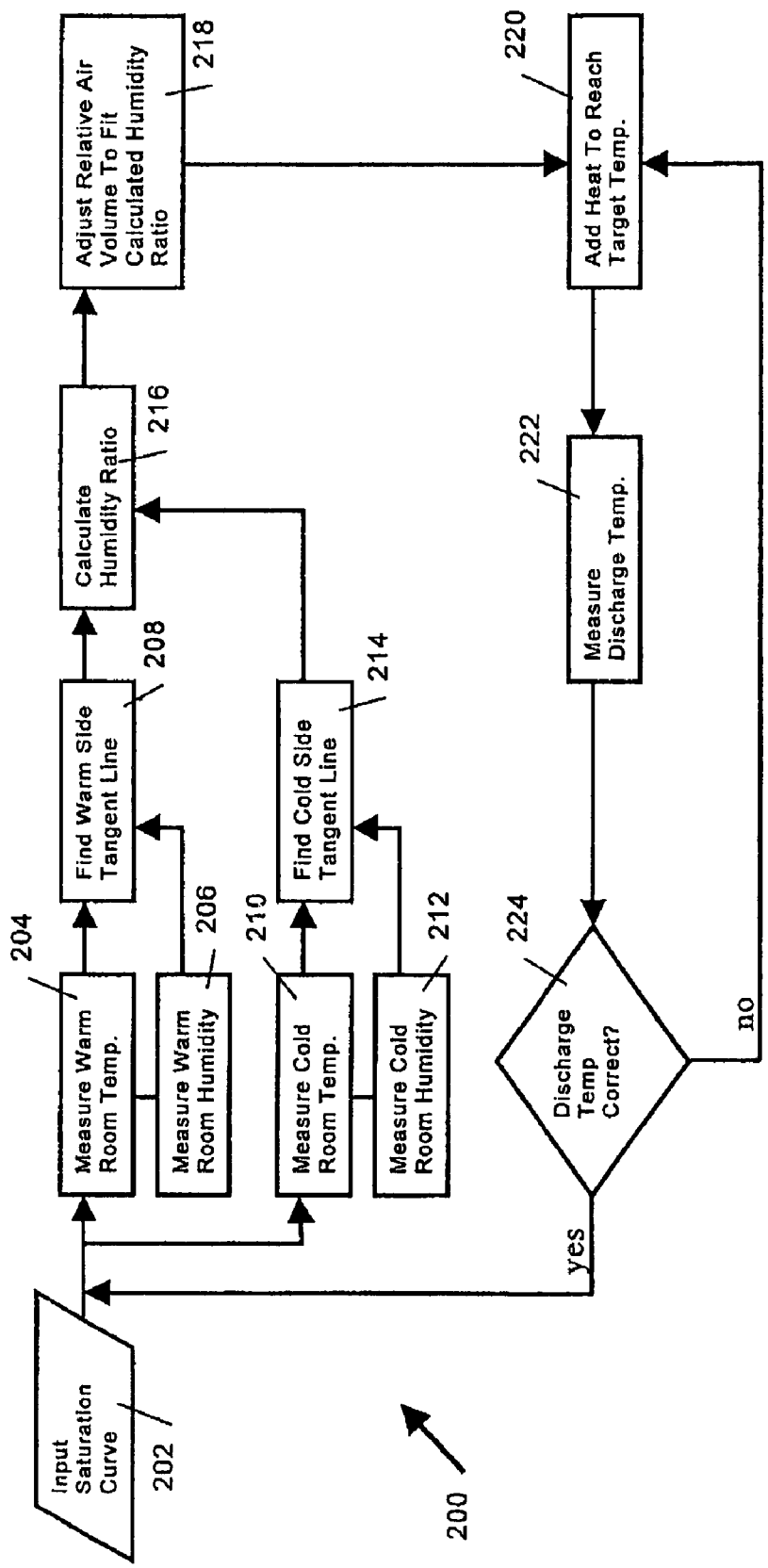
FIG. 10 shows a flowchart of another exemplary embodiment of a method of controlling an air curtain arrangement by varying airflow among separate air curtains.

FIG. 10 shows a flowchart of another exemplary embodiment of a method 200 of controlling an air curtain arrangement 10 by varying airflow among the separate air curtains AA, BB, CC. Airflow volume may be varied, for example, by using variable-speed fans in one or more of the air curtains AA, BB, CC. Depending upon the conditions, the control unit 50 may adjust the relative air speed of the fans dynamically to adjust the humidity ratio to minimize the amount of heat that the first air curtain AA must add, thereby optimizing the efficiency of the air curtain arrangement 10. For simplicity, each of the previous examples of double and triple air curtains are illustrated as having substantially the same air discharge volume for each air curtain AA, BB, CC (e.g., varies less than 25%). The humidity ratio lines $HR_1$, $HR_2$, $HR_3$, $HR_4$, defined on the example psychrometric charts depend upon each air curtain's relative volume of airflow.

In the embodiment of FIG. 10, a saturation curve is input 202 into the control unit 50. Warm room temperature and humidity are measured 204, 206. Cold room temperature and humidity are measured 210, 212. A warm side tangent line is determined 208 based on the warm side temperature and humidity, and a cold side tangent line is determined 214 based on the cold side temperature and humidity. In the example of FIG. 10, a humidity ratio is calculated 216 as a horizontal line on the psychrometric chart passing through the point defined by the intersection of the warm and cold side tangent lines (point 2* in FIG. 11). The relative air volume of the air curtains (e.g., AA, BB, CC) is adjusted 218 to create a humidity ratio equal to the ratio that was calculated 216. Heat is added 220** to reach a target temperature based on the calculated humidity ratio. By adjusting the relative air discharge volumes at the air curtains (e.g., AA, BB, CC) and thereby adjusting the humidity ratio, the required amount of heat may be decreased or even minimized.

As with the embodiment described with respect to FIG. 2, heat added to arrangement may be adjusted dynamically. An air discharge temperature is measured 222. If the air discharge temperature is the correct target temperature ("yes" branch at block 224), then the method 200 repeats itself. If the air discharge temperature is not correct ("no" branch at block 224), then the correct amount of heat is added 220. As with other embodiments described herein, the amount of heat added may include a buffer (e.g., 10 degrees above the calculated temperature) to ensure that the operating conditions of the air curtain arrangement remain below the tangent line to the saturation curve.

In one embodiment, the airflow is adjusted dynamically based upon changing conditions in the air curtain arrangement 10. Airflow may be adjusted, for example, by controlling variable-speed fans in one or more of the individual air curtains AA, BB, CC. As the warm side or cold side tangent lines change, for example, the desired humidity ratio changes thereby requiring adjustment of the relative volumetric airflow of the individual air curtains AA, BB, CC. Also, airflow sensors (not shown) may be used to monitor the actual airflow across the air curtain arrangement 10 and to adjust fan speed (or other airflow control) based on the measured airflow.

Figure 11:
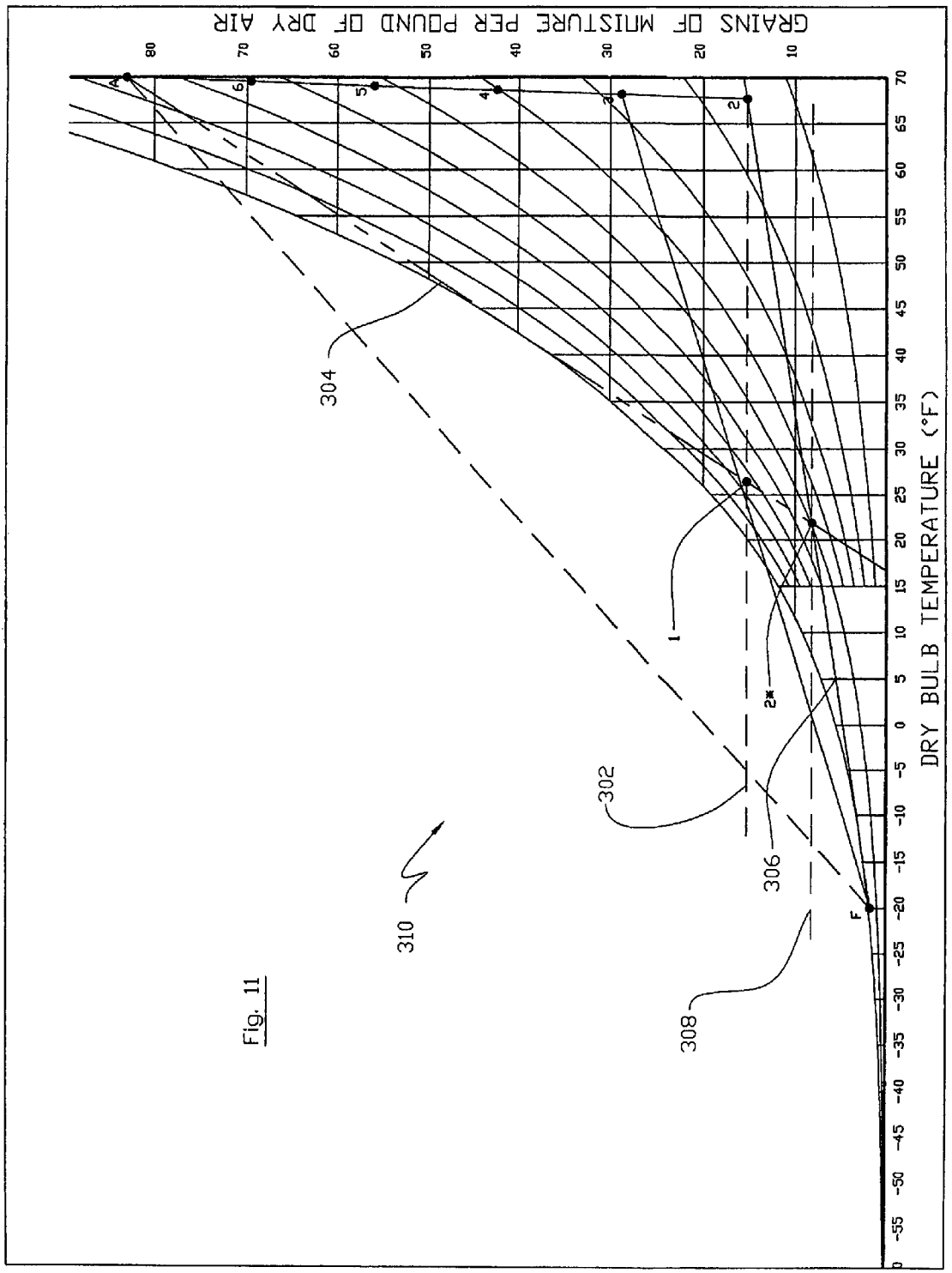
FIG. 11 shows an example psychrometric chart for a triple air curtain arrangement illustrating the method of FIG. 10.

FIG. 11 shows an example psychrometric chart 310 for a triple air curtain arrangement illustrating the method 200 of FIG. 10. The example air curtain arrangement is positioned between a freezer F at −20 degrees Fahrenheit and an anteroom A at 70 degrees Fahrenheit. The warm side tangent line 304 and the cold side tangent line 306 are shown on the chart 310. Dashed line 302 represents the even airflow humidity ratio. This would be the humidity ratio of the arrangement if each of the three air curtains AA, BB, CC had a fixed and equal airflow. Points 1 and 2 represent the intersections of the even airflow humidity ratio line 302 with the warm side tangent line 304 and the cold side tangent line 306, respectively. At low freezer temperatures, such as the −20 degrees Fahrenheit of this example, the cold side tangent line 306 begins to flatten more noticeably. As a result, the temperature difference between points 1 and 2 is larger. To avoid ice formation at this humidity ratio, sufficient heat would have to be added based on point 2, as the larger of the two temperatures 1, 2. In this example, point 2 is at a much warmer temperature than point 1, which would require addition of substantial heat.

To minimize the amount of heat required to be added, relative airflow in the air curtains AA, BB, CC is adjusted to lower the humidity ratio line closer to (or, in the embodiment shown, exactly at) the intersection of the warm side tangent line 304 and the cold side tangent line 306. The new humidity ratio line is illustrated as a dashed line 308, and passes through the intersection point 2*. In the embodiment of FIG. 11, the humidity ratio is lowered by increasing the airflow of the freezer-side air curtain AA relative to at least one of the other two air curtains BB, CC. As a result, less heat is required to be added to bring the air curtain arrangement to the target temperature 2*, than would be required to reach point 2, or even point 1 in this example.

In other embodiments, the humidity ratio is adjusted from an even flow humidity ratio, but is not lowered all the way to the intersection point 2*. In such embodiments, points 1 and 2 are separate points along the humidity ratio line, as described with respect to FIGS. 4 and 5. Heat is added to the arrangement based on the larger of points 1 and 2, as described with respect to FIG. 3. In this manner, the efficiency of the arrangement is increased even though the humidity ratio is not set all the way to the intersection point of the cold and warm side tangent lines.

Figure 12:
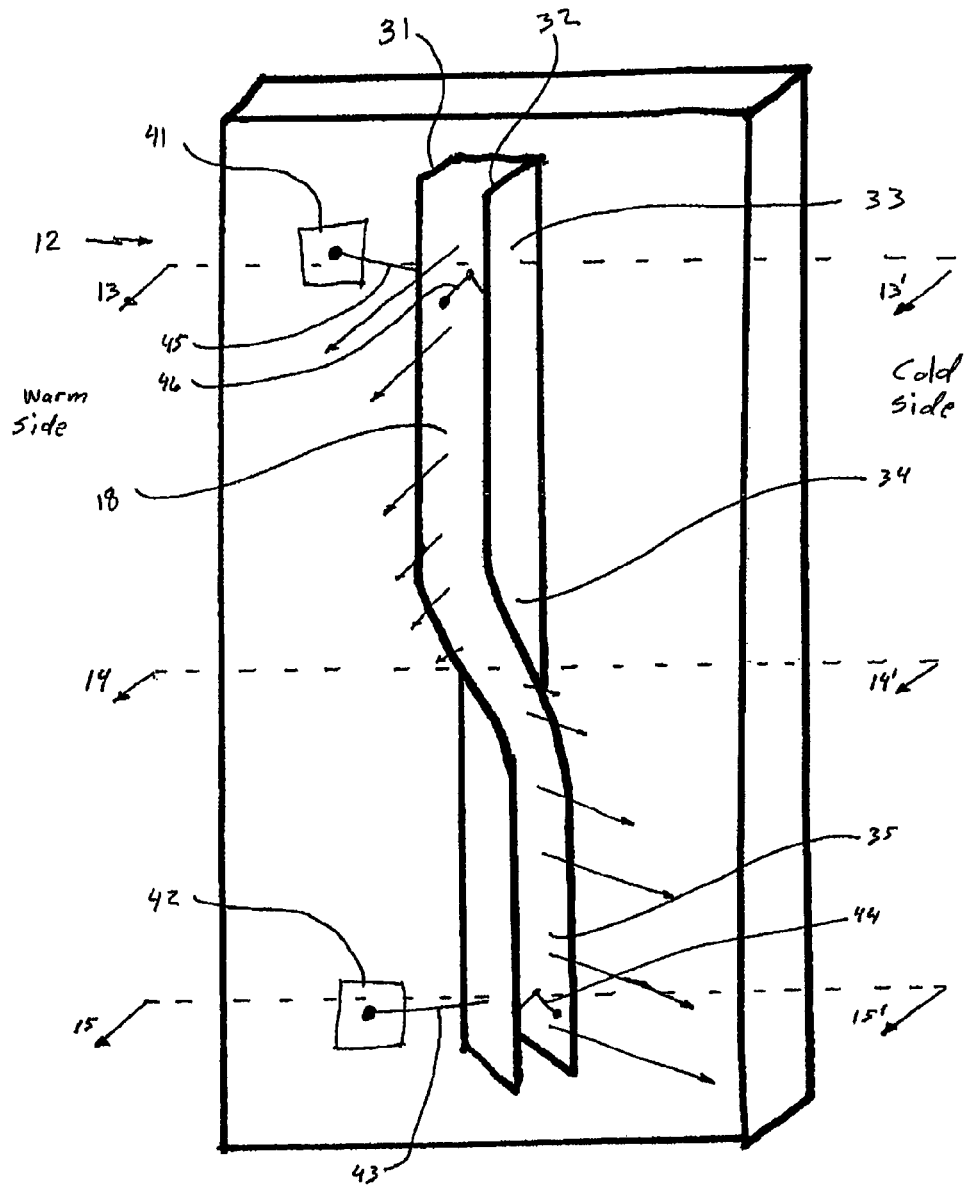
FIG. 12 shows a perspective view of a discharge plenum of an air curtain, such as the air curtain AA in the arrangement shown in FIG. 1, having an adjustable discharge nozzle.

FIG. 12 shows a perspective view of a discharge plenum 12 of a horizontal air curtain, such as the air curtain AA in the arrangement 10 shown in FIG. 1, having an adjustable discharge nozzle 18. In the embodiment of FIG. 12, the discharge nozzle 18 comprises parallel blades 31, 32 that run along the length of the discharge plenum 12. The blades may be formed, for example, of flexible sheet metal and may be positioned to direct discharged air in different directions at different portions of the discharge nozzle. For efficient operation of the air curtain arrangement (e.g., 10 in FIG. 1), it may be desirable to discharge air toward the relatively warm side near the top of the discharge plenum 12 and toward the relatively cold side for discharged air near the bottom of the plenum 12. This counteracts the natural tendency of cold air to exfiltrate the relatively cold room near the floor and of warm air to infiltrate the relatively cold room near the ceiling (or top of the air curtain). In the example of FIG. 12, an upper portion 33 of the discharge nozzle 18 directs discharged air toward the relatively warm side. A lower portion 35 of the discharge nozzle 18 directs discharged air toward the relatively cold side. A middle portion of the discharge nozzle 18 directs air generally straight across the doorway.

The embodiment of the discharge plenum 12 shown in FIG. 12 includes two actuators 41, 42 (e.g., motors) that control the direction of air discharged through the nozzle 18. The actuators 41, 42 control air direction by moving the blades 31, 32 toward or away from the relatively warm side. In the embodiment shown in FIG. 12, linkage 42, 43, 44, 45 connects the actuators 41, 42 to the blades 31, 32, and the blades 31, 32 to each other. The blades 31, 32 move in response to the actuators 41, 42 to thereby change the direction of the discharged air. In the embodiment of FIG. 12, the blades 31, 32 of the discharge nozzle 18 may be formed of continuous pieces of flexible sheet metal that permit a lower portion 35 of the nozzle 18 to move independently of an upper portion 33 of the discharge nozzle 18. Other embodiments of the nozzle 18 may also permit independent movement of different portions of the discharge nozzle 18. For example, the discharge nozzle 18 may be formed of rigid blades (not shown) that are hingedly connected to the supply plenum 12 and are separated into two or more portions (e.g., upper and lower portions) that move independently.

Figure 13:
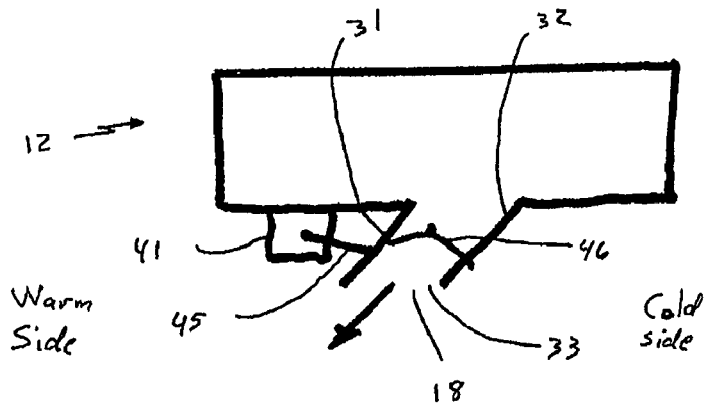
FIG. 13 shows a cross-section view of an upper portion of the discharge plenum shown in FIG. 12, taken along the line 13-13'.

FIG. 13 shows a cross-section view of an upper portion of the discharge plenum 12 shown in FIG. 12, taken along the line 13-13′. The upper portion 33 of the discharge nozzle 18 directs air generally toward the relatively warm side to counteract air from the warm side attempting to infiltrate the relatively cold side.

Figure 14:
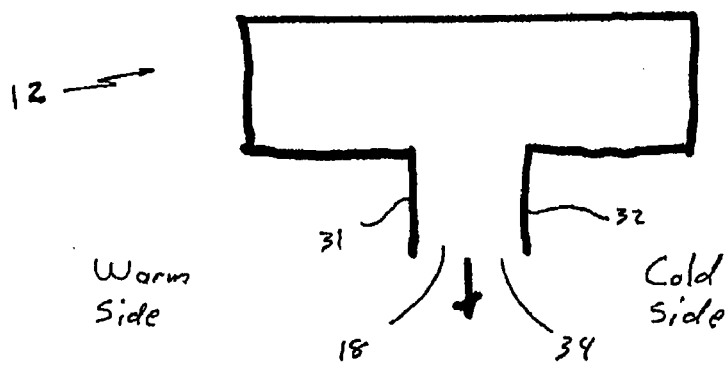
FIG. 14 shows a cross-section view of a mid-portion of the discharge plenum shown in FIG. 12, taken along the line 14-14'.

FIG. 14 shows a cross-section view of a mid-portion of the discharge plenum 12 shown in FIG. 12, taken along the line 14-14′. The mid-portion 34 of the discharge nozzle 18 directs air generally straight across the doorway, in this embodiment.

Figure 15:
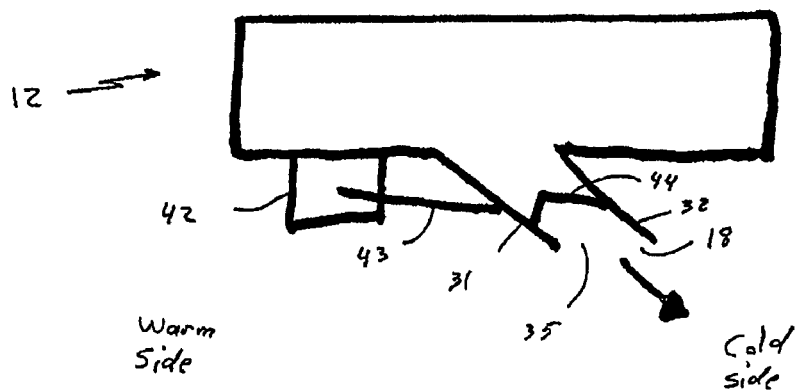
FIG. 15 shows a cross-section view of a lower portion of the discharge plenum 12 shown in FIG. 12, taken along the line 15-15'.

FIG. 15 shows a cross-section view of a lower portion of the discharge plenum 12 shown in FIG. 12, taken along the line 15-15′. The lower portion 35 of the discharge nozzle 18 directs air generally toward the relatively cold side to counteract air from the cold side attempting to exfiltrate the relatively cold side. In each of the examples of FIGS. 13, 14, and 15, the exact position of the blades 31, 32 may be adjusted by one or more actuators (e.g., 41, 42). Spacing between the blades 31, 32 may vary at different points along the length of the blades 31, 32, and may be adjusted by the linkage 44, 46 therebetween.

Figure 16:
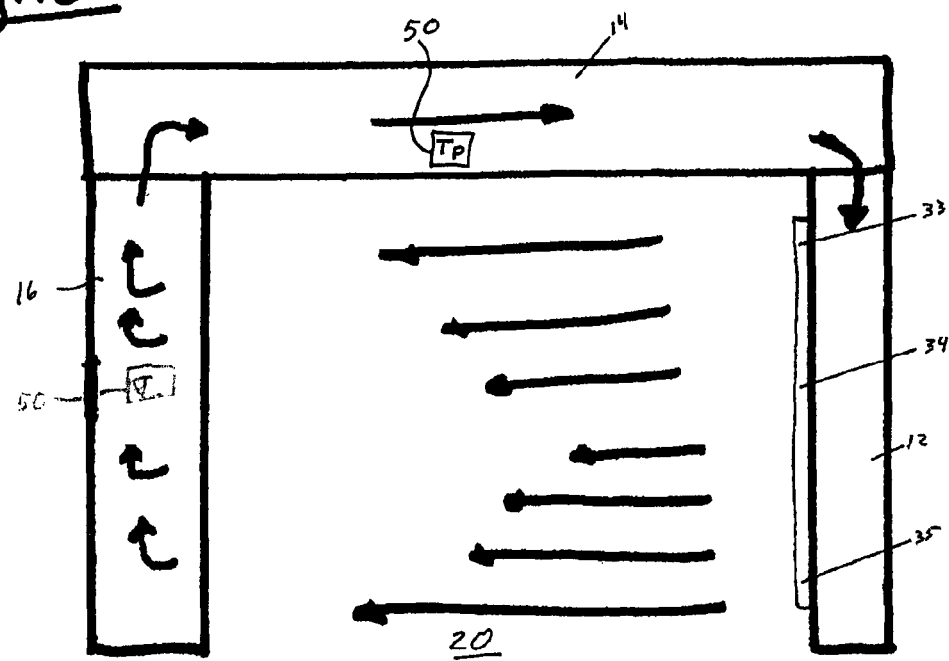
FIG. 16 shows an elevation view of an air curtain arrangement.
Figure 17:
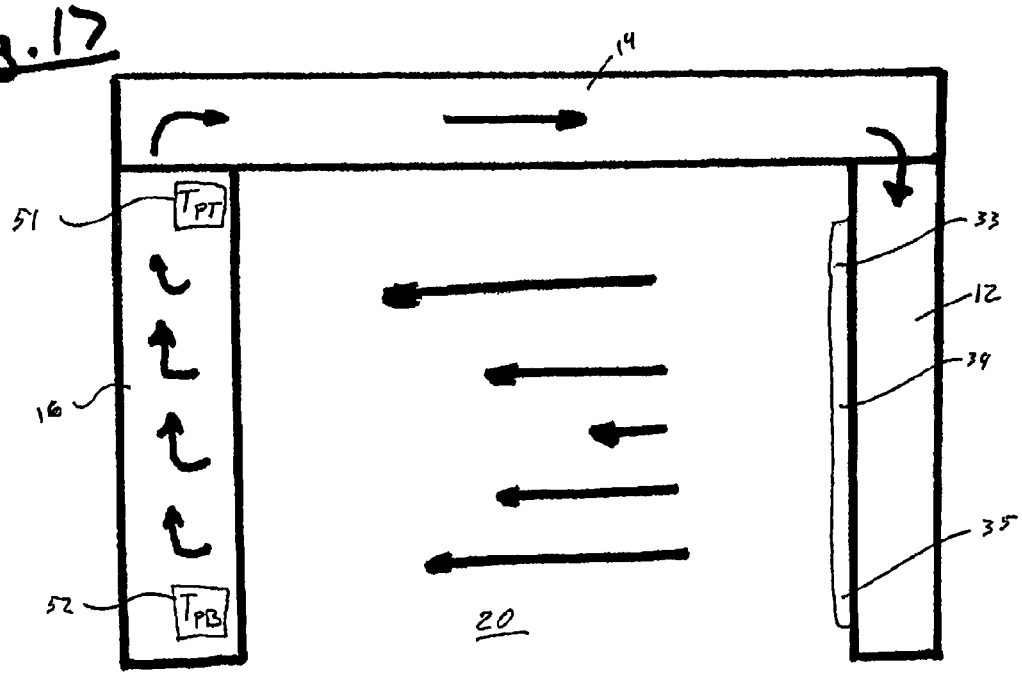
FIG. 17 shows an elevation view of another embodiment of an air curtain arrangement.

FIGS. 16 and 17 show elevation views of an air curtain arrangement, such as the arrangement AA shown in FIG. 1, including temperature sensors 50, 51, 52 in the return air duct 16 and/or intermediate air duct 14. Air is discharged by the nozzle 18 across the doorway 20 and received at the air return duct 16. The embodiment of FIG. 16 includes a single plenum temperature sensor 50 that measures a temperature T(p) of the air received at the return duct 16. In this example, the plenum temperature sensor 50 is located in the intermediate air duct 14. The embodiment of FIG. 17 includes two return air temperature sensors 51, 52 that measure temperatures T(pt), T(pb) of discharged air received at the top and bottom of the return air duct 16. In one embodiment, both sensors 51, 52 are positioned immediately near the inlet aperture 19 so that they sense temperatures of discharged air that is received at the inlet aperture 19 at different points, before the received air mixes in the return air duct 16. Although the sensors 51, 52 are illustrated as being located in the return air duct 16 in the embodiment of FIG. 17, in another embodiment they may be located outside of the return air duct 16 or otherwise situated so that the sensors (e.g., the top sensor 51) accurately measures the air temperature received at the top of the plenum (T(pt)) before the air received at the top of the return air duct 16 is commingled with air received at the bottom of the return air duct 16. As indicated by the air discharge arrows in FIGS. 16 and 17, the velocity of the discharged air stream may be greater near the top and bottom of the doorway 20, for example, by decreasing the width between the blades 31, 32 near the mid-portion 34 of the discharge nozzle 18 or using a damper.

Figure 18A:
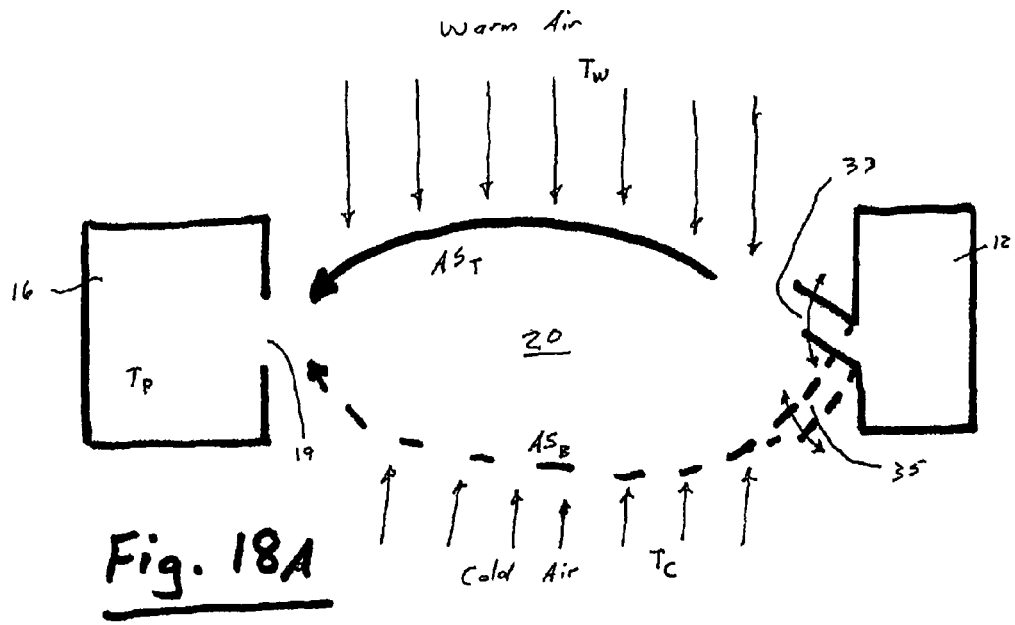
FIGS. 18A and 18B illustrate adjustment of the air discharge nozzle to change the direction of airflow.
Figure 18B:
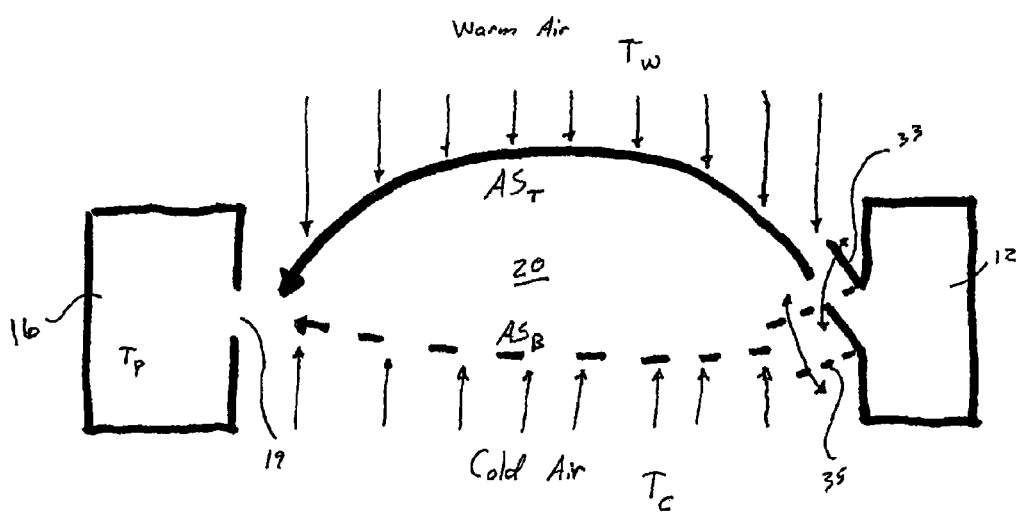

FIGS. 18A and 18B illustrate adjustment of the air discharge nozzle 18 to change the direction of airflow. Top and bottom portions $AS_T$, $AS_B$ of an air stream are directed across the doorway 20. As shown, the top portion of the air stream $AS_T$ is angled more toward the warm side than the bottom portion of the air stream $AS_B$, which is angled toward the cold side. This counteracts the warm side air and cold side air (at respective temperatures $T_w$ and TO. The direction of discharge may be adjusted, as described herein. Efficiency of air curtain operation depends in part on the direction of the discharged air. Discharged air may be heated by a heater, as described herein. Only a portion of the discharged air is received at the return plenum 16. Because energy is added to heat the air stream, it is generally desirable for the return air plenum 16 to capture as much of the air stream as possible. This may be achieved by adjusting the direction of air discharge from the nozzle 18, for example, by using one or more actuators (e.g. 41, 42 in FIG. 12) to dynamically control the blades 31, 32. Comparing FIGS. 18A and 18B, for example, the nozzle 18 generally discharges the air stream more toward the relatively warm side in FIG. 18B than in FIG. 18A, due to the operating conditions. The present invention senses operating conditions and automatically directs the discharged air stream based upon the sensed conditions in order to maintain the portion of the air stream that is received at the inlet aperture 19.

Figure 19:
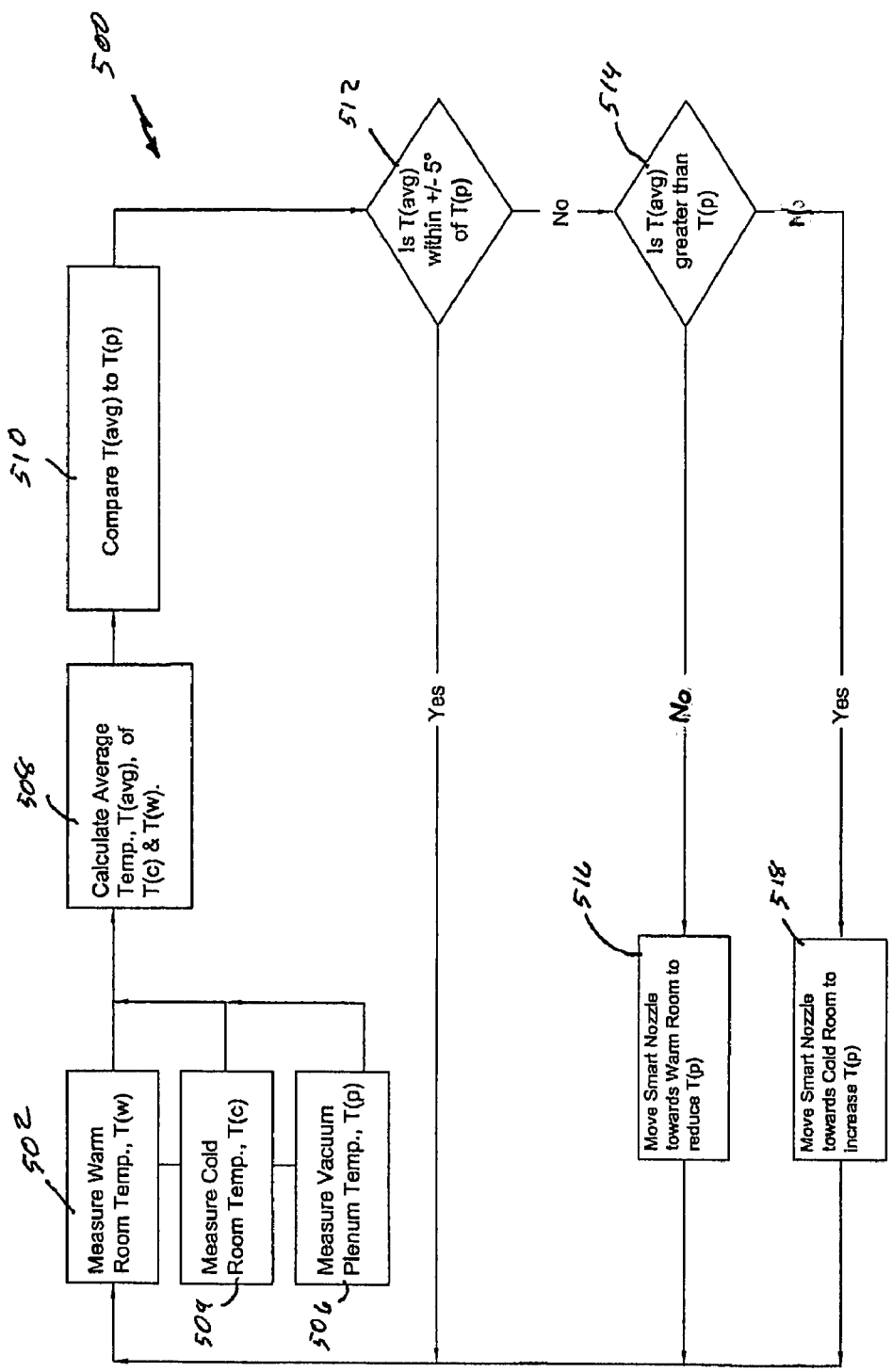
FIG. 19 shows a flowchart of one embodiment of a method for controlling direction of airflow discharged by an air curtain arrangement across a doorway.

FIG. 19 shows a flowchart of one embodiment of a method 500 for controlling direction of airflow discharged by an air curtain arrangement across a doorway 20. The embodiment of FIG. 19 applies to an air curtain arrangement 10 in which position of the air discharge nozzle is controlled by a single actuator (e.g. 41, 42 in FIG. 12), such as a motor that moves blades 31, 32 of the discharge nozzle 18. For example, the entire nozzle 18 may move laterally in response to an actuator (e.g. 41, 42 in FIG. 12), controlled according to the method 500 in the example of FIG. 19. Other embodiments may control movement of the discharge nozzle 18 using more than one actuator, for example, by using two actuators (e.g. 41, 42 in FIG. 12) positioned on different portions of the discharge nozzle 18, which operate independent of each other.

A temperature T(w) of a relatively warm room is measured 502. A temperature T(c) of a relatively cold room is measured 504. These temperatures T(w), T(c) may be measured, for example, by using temperature sensors (not shown) located in the relatively warm and cold rooms, by retrieving climactic data from a remote source, such as the National Weather Service for outdoor loading dock applications, or by retrieving ambient air temperatures from a third party via a computer network such as the Internet. A temperature of air returned to the return plenum T(p) is measured 506. Plenum temperature T(p) may be measured, for example, by using a temperature sensor located in or near the return air duct 16 or the intermediate air duct 14 of the air curtain AA. An average temperature T(avg) is determined 508 based upon the temperatures of the relatively warm and cold side rooms T(w), T(c) (e.g., [T(w)+T(c)]/2), and the average temperature T(avg) is compared 510 to the plenum temperature T(p). If the average temperature T(avg) is within a specified margin (e.g., +/−5 degrees F.) of the plenum temperature T(p) ("yes" branch at block 512), then the method 500 feeds back and the temperatures are again measured 502, 504, 506.

If the average temperature T(avg) differs from the plenum temperature T(p) by the specified margin ("no" branch at block 512), then this indicates that the discharged airflow might not be directed in the desired manner. In that case, if the average temperature T(avg) exceeds the plenum temperature T(p), ("yes" branch at block 514), then the discharge nozzle 18 is directed 518 further toward the relatively cold room, which should increase the plenum temperature T(p). If the average temperature T(avg) is less than the plenum temperature T(p), ("no" branch at block 514), then the discharge nozzle 18 is directed 516 further toward the relatively warm room, which should decrease the plenum temperature T(p). The method 500 then feeds back and the temperatures are again measured 502, 504, 506. In one embodiment, the method 500 may feed back continuously or at regular intervals (e.g., once per hour, once per minute, or more frequently) to move the discharge nozzle dynamically, as temperatures change throughout the day.

Figure 20:
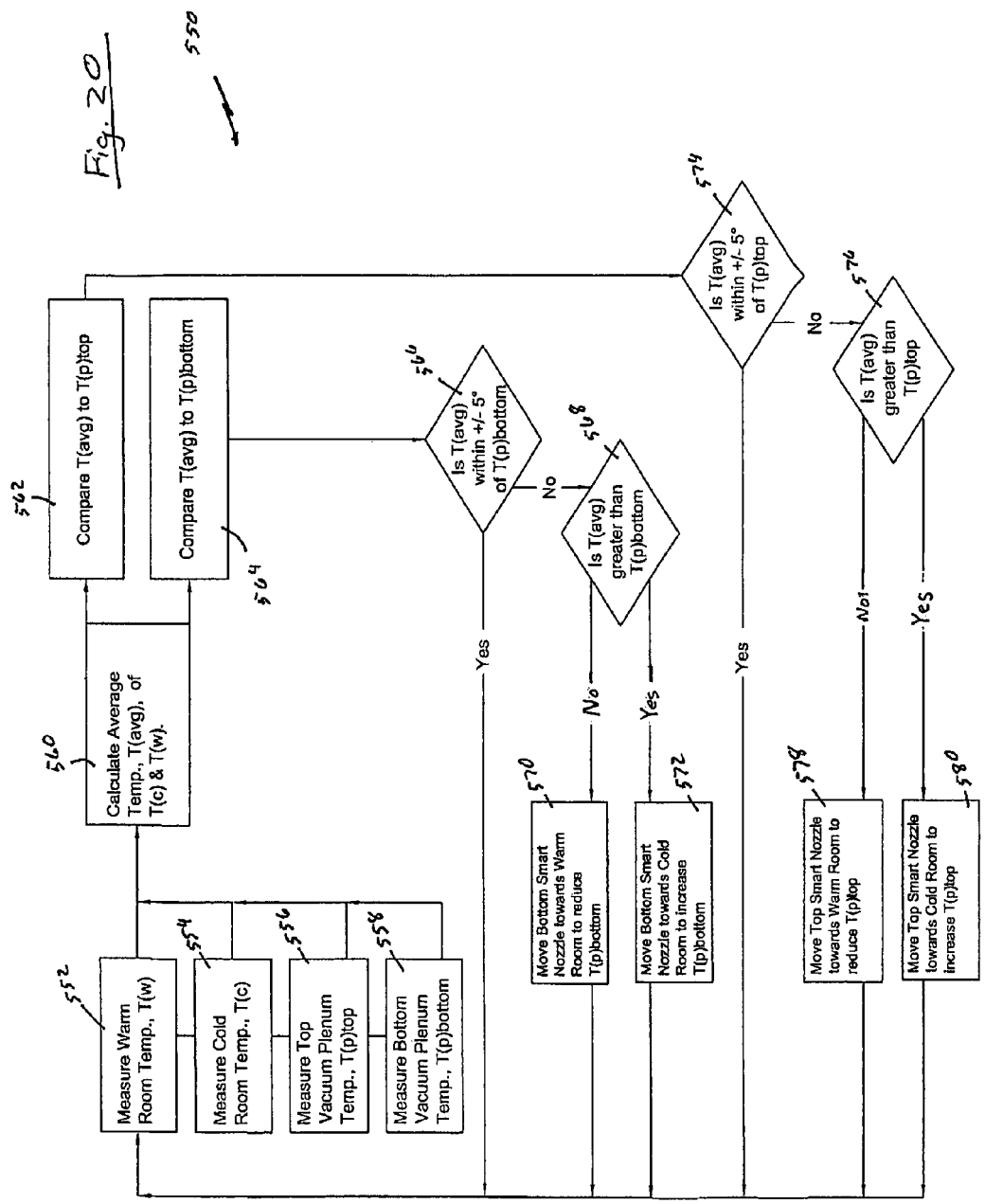
FIG. 20 shows a flowchart of another embodiment of a method for controlling discharge airflow direction of an air curtain, having two independently-operated actuators that direct discharged airflow at upper and lower portions of the outlet aperture.

FIG. 20 shows a flowchart of another embodiment of a method 550 for controlling discharge airflow direction of an air curtain, having two independently-operated actuators that direct discharged airflow at upper and lower portions, respectively, of the air curtain. The method 550 of FIG. 20 may be implemented, for example, using two separate actuators 41, 42 as shown in FIG. 12 to independently move an upper portion 33 and a lower portion 35 of the discharge nozzle 18.

In the exemplary method 550 of FIG. 20, the relatively warm and cold room temperatures are measured 552, 554 (or otherwise determined), as described with respect to FIG. 19. The air curtain embodiment of FIG. 20 includes two plenum temperature sensors (e.g. 51, 52 in FIG. 17), one positioned near the top of the return air inlet 19 and the other near the bottom of the return air inlet 19, for example, as shown in FIG. 17. Using these sensors, top and bottom plenum temperatures T(pt), T(pb) are measured 554, 556. An average temperature T(avg) is calculated 560 as an average of the temperatures of the relatively cold and warm rooms T(c), T(w). The average temperature is then compared separately to the top and bottom plenum temperatures T(pt), T(pb), and upper and lower portions of the discharge nozzle 18 are moved in response thereto.

The average temperature T(avg) is compared 564 to the bottom plenum temperature T(pb) (or T(p) bottom). If the average temperature T(avg) is within a specified margin of the bottom plenum temperature T(pb) ("yes" branch at block 566), then the method 550 feeds back and temperatures are again measured 552, 554, 556, 558. If the average temperature T(avg) differs from the bottom plenum temperature T(pb) by more than the specified margin ("no" branch at block 566), then the bottom portion 35 of the discharge nozzle 18 is moved 570 toward the warm side, if the average temperature T(avg) is less than the bottom plenum temperature T(pb) ("no" branch at block 568). The bottom portion 35 of the discharge nozzle 18 is moved 572 toward the cold side, if the average temperature T(avg) is greater than the bottom plenum temperature T(pb) ("yes" branch at block 568). The method 550 then feeds back and temperatures are again measured 552, 554, 556, 558.

Independent of the control of the bottom portion 35 of the discharge nozzle 18, the average temperature T(avg) is also compared 562 to the top plenum temperature T(pt). If the average temperature T(avg) is within a specified margin of the top plenum temperature T(pt) ("yes" branch at block 574), then the method 550 feeds back and temperatures are again measured 552, 554, 556, 558. If the average temperature differs from the top plenum temperature T(pt) by more than the specified margin ("no" branch at block 574), then the top portion 33 of the discharge nozzle 18 is moved 578 toward the warm side, if the average temperature T(avg) is less than the top plenum temperature T(pt) ("no" branch at block 576). The top portion 33 of the discharge nozzle 18 is moved 580 toward the cold side, if the average temperature T(avg) is greater than the top plenum temperature T(pt) ("yes" branch at block 576). The method 550 then feeds back and temperatures are again measured 552, 554, 556, 558.

Figure 21:
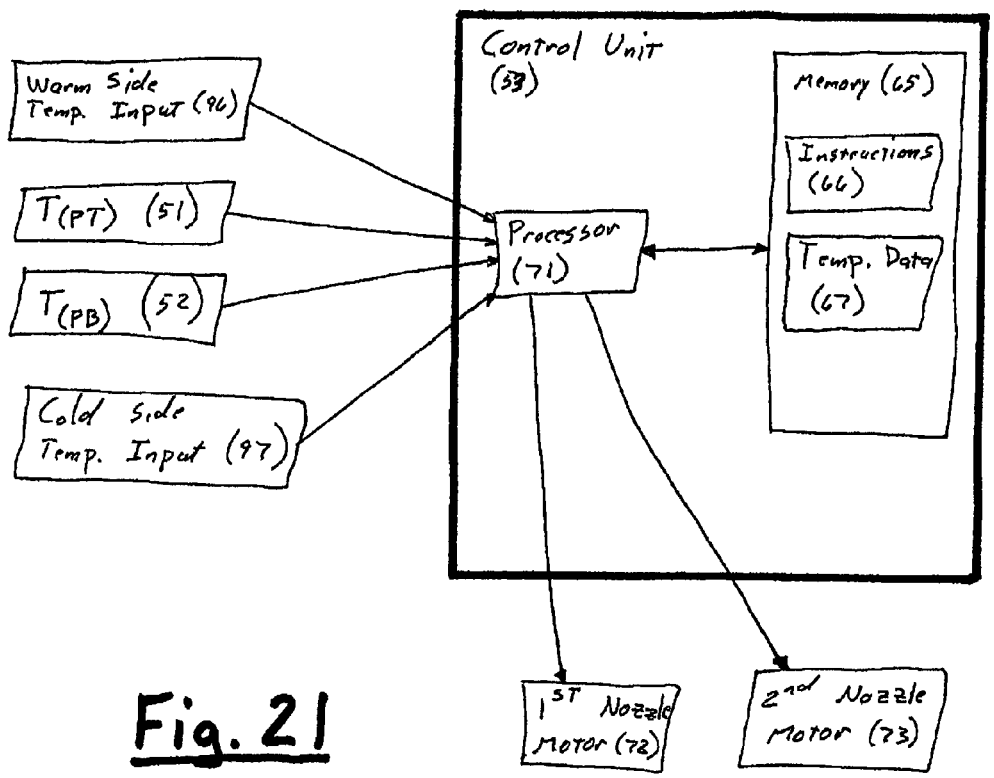
FIG. 21 shows a block diagram of one embodiment of a control unit that may be used to implement the method described with respect to FIG. 20.

FIG. 21 shows a block diagram of one embodiment of a control unit 53 that may be used to implement the method 550 described with respect to FIG. 20. The air direction control unit 51 may be a part of the control unit 50 described with respect to FIG. 6, or may be a separate unit. The control unit 53 includes a processor 71 that interfaces with a storage arrangement, such as memory 65. The memory 65 stores instructions 66 for performing a method of controlling direction of an air stream discharged from a nozzle 18, such as the method 550 described with respect to FIG. 20. The memory 65 also stores temperature data 67 gathered by operating condition sensors, such as the temperature sensors 96, 97, 51, 52 illustrated in the embodiment of FIG. 21. The processor 71 receives inputs from temperature sensors 96, 97, 51, 52 that sense top and bottom plenum temperatures T(pt), T(pb), a warm side temperature T(w), and a cold side temperature T(c), respectively. The processor 71 stores input data from the sensors 96, 97, 51, 52 as temperature data 67 in memory 65. The processor 71 executes instructions 65 based upon the temperature data 67, which cause the processor 71 to send control signals to motors 72, 73 (or other movers) that control movement of the discharge nozzle 18, for example, by moving blades 31, 32 of a nozzle 18 such as the one described with respect to FIGS. 12-15. The control unit 53 embodiment of FIG. 21 controls an air curtain unit AA capable of independently moving separate portions of the discharge nozzle 18 (e.g., top and bottom, as described with respect to FIGS. 12-15). In other embodiments, a single mover may control airflow direction.

Figure 22:
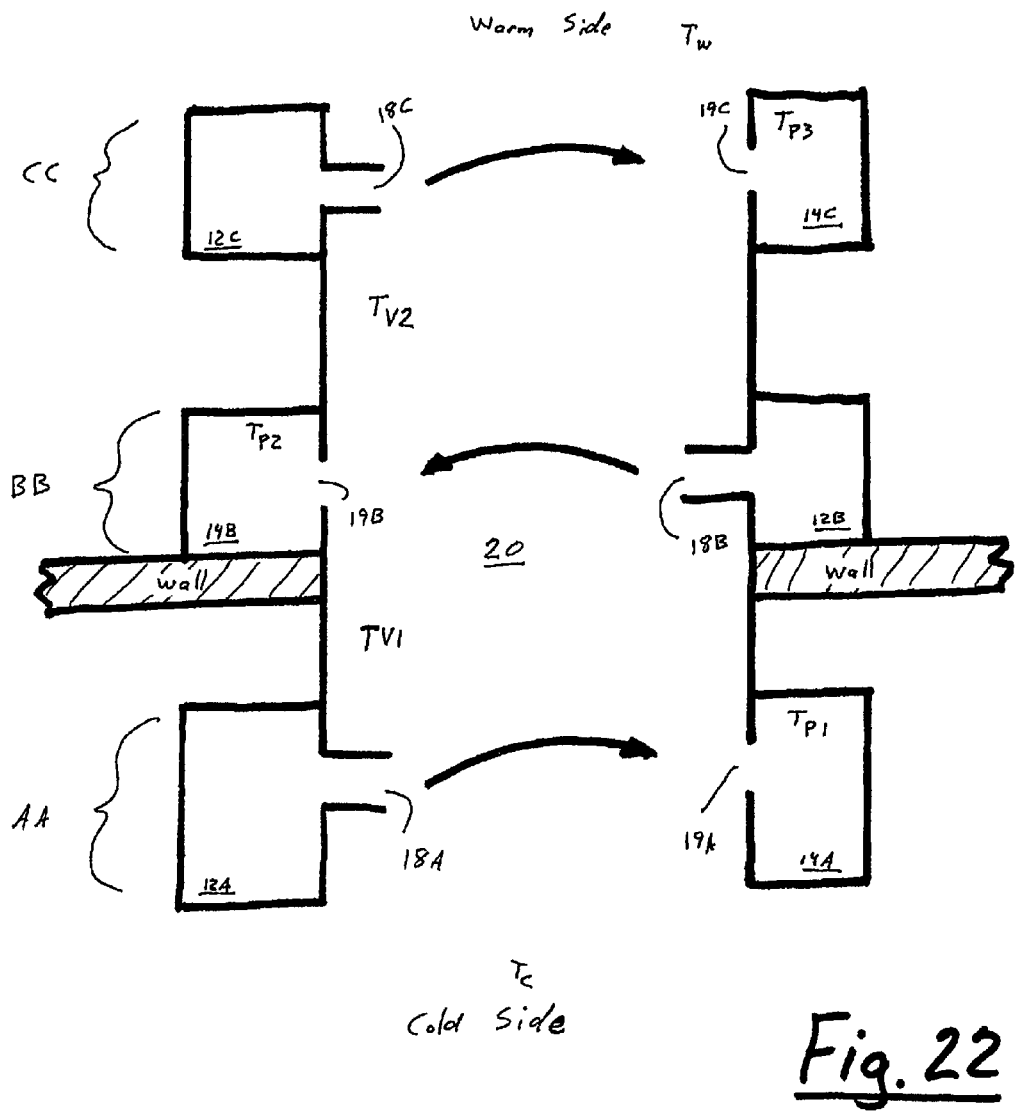
FIG. 22 shows a top view of a triple air curtain arrangement.

Although the air direction control system of the present invention has been described with respect to embodiments of a single air curtain unit, the invention may include an air curtain arrangement including multiple air curtain units (e.g., AA, BB in FIG. 1). FIG. 22 shows a top view of a triple air curtain arrangement, illustrating the discharge air control system described herein, such as the arrangement illustrated in the block diagram of FIG. 7. The arrangement includes three air curtains AA, BB, CC positioned across a doorway 20 that separates a warm side from a cold side.

Each air curtain unit AA, BB, CC includes a discharge nozzle 18A, 18B, 18C formed from protruding blades that direct air across the doorway. Adjacent air curtain units (e.g., AA, BB) direct air across the doorway 20 in generally opposite directions. In one embodiment, the nozzles 18A, 18B, 18C on each unit AA, BB, CC may be controlled separately to control the direction of discharged air. Each unit AA, BB, CC may use motors (not shown) or other movement devices to change the direction of discharge airflow dynamically, based upon operating conditions, for example, as described with respect to FIGS. 12-15.

As with the methods 500, 550 described with respect to FIGS. 19 and 20, the multiple air curtain arrangement compares temperatures of opposing sides of an air curtain unit (e.g., AA) with a return plenum temperature T(p) and iteratively positions the discharge nozzle 18 to minimize differences between the plenum temperature T(p) and the average of the temperatures on opposing sides of the air curtain unit AA. In the multiple air curtain arrangement, however, the temperatures on opposing sides of each air curtain unit AA, BB, CC include at least one intermediate temperature that is measured between adjacent air curtain units. Sensors (not shown) measure intermediate temperatures T(v1) and T(v2) between air curtain units AA, BB and BB, CC, respectively. In operation, the method 500 described with respect to FIG. 19 is modified for the first air curtain unit AA to compare the plenum temperature T(p1) of the first air curtain unit AA with the average T(avg1) of the cold side temperature T(c) and the first intermediate temperature T(v1), rather than the warm side temperature T(w). The plenum temperature T(p2) of the second air curtain unit BB is compared to the average T(avg2) of the first intermediate temperature T(v1) and the second intermediate temperature T(v2). The plenum temperature T(p3) of the third air curtain unit CC is compared to the average T(avg3) of the warm side temperature T(w) and the second intermediate temperature T(v2). In one embodiment, the nozzles 18A, 18B, 18C are moved until the plenum temperatures T(p1), T(p2), T(p3) are equal to (or within a specified margin of) the averages of the temperatures on either side of the air curtain unit AA, BB, CC.

One or more units AA, BB, CC in a multiple air curtain arrangement, such as the arrangement shown in FIG. 22, may also measure more than one plenum temperature for each return plenum 14A, 14B, 14C. For example, each unit AA, BB, CC may measure top and bottom plenum temperatures as described with respect to FIGS. 17 and 20, and independently control separate portions of the discharge nozzles 18A, 18B, 18C. Although the discharge nozzle 18 has been described herein as having two blades, one skilled in the art will recognize that various means may be used as a discharge nozzle to discharge air across the doorway 20 and various means, other than a motor and linkage, may be used to control direction of the discharged air. In one embodiment, the discharged air may be directed within a range of +/−40 degrees of being straight across the doorway 20. Other embodiments may permit greater or lesser change in direction.

Figure 23:
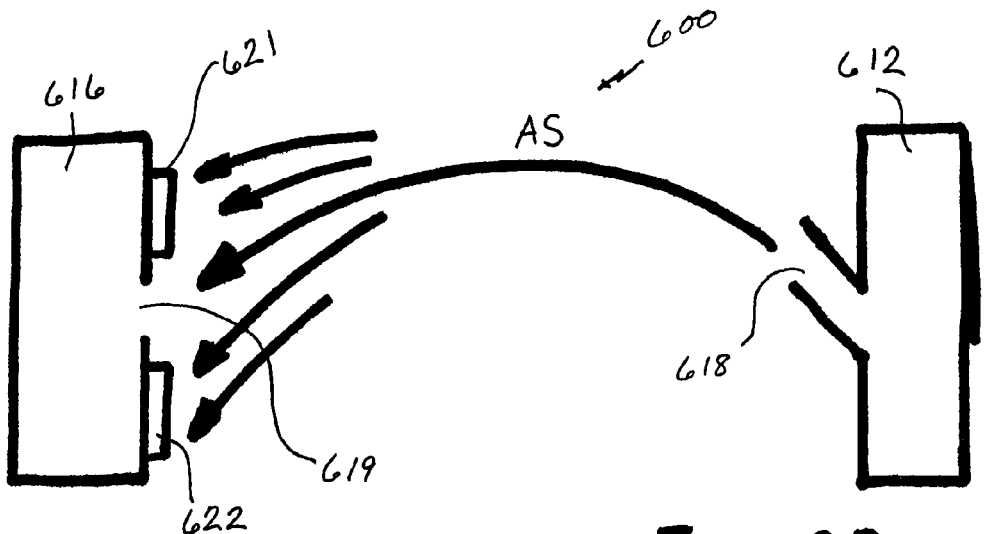
FIG. 23 shows a top view of another embodiment of an air curtain.

FIG. 23 shows a top view of another embodiment of an air curtain 600. The supply plenum 12 discharges an air stream AS through the discharge nozzle 618. A portion of the air stream AS is received at the inlet aperture 619 of the return air duct 616. The return air duct 616 in this embodiment includes one or more air stream sensors 621, 622, such as thin film tactile sensors. In the embodiment shown, the air stream sensors 621, 622 are positioned on opposite sides of the inlet aperture 619. The air stream sensors 621, 622 sense a portion of the air stream that is received at the air return duct 616 away from the inlet aperture 619. The air stream sensors 621, 622 are used to sense the portion of the air stream AS that is received by the inlet aperture 619, and the control unit (e.g., 53 in FIG. 21) controls the direction of the discharge nozzle 618 or the velocity of the air stream AS, or both, so as to maximize the portion of the air stream AS received at the inlet aperture 619. Because the entire air stream 619 is not received at the inlet aperture 619, a portion of the air stream AS will contact the sensors 621, 622 on either side of the inlet aperture 619. In one embodiment, the air stream direction or velocity, or both, is directed such that a substantially equal portion of the air stream AS is received at the sensors on opposing sides of the inlet aperture 619. The air stream sensors 621, 622 may be used to control the air discharge nozzle 6128 in connection with a temperature method 500, 550 described with respect to FIGS. 19, 20, or may be used separately.

Figure 24:
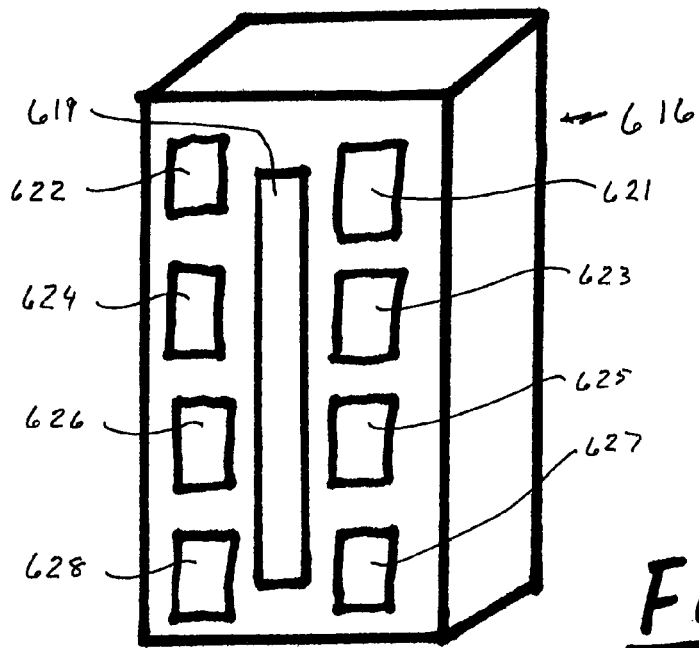
FIG. 24 shows a perspective view of the air return duct shown in FIG. 23.

FIG. 24 shows a perspective view of the air return duct 616 shown in FIG. 23. The embodiment shown includes a plurality of air stream sensors 621-628 positioned on opposing sides of the inlet aperture 619. The multiple sensors 621-628 may be used together to maximize the portion of the air stream AS that is received at the inlet aperture 619, for example, by averaging values of the portions of the sensed air stream AS or by providing inputs to the control unit (e.g., 53 in FIG. 21) to control multiple actuators (e.g., 41, 42 in FIG. 12) of the air discharge nozzle 618. One skilled in the art will recognize that more or fewer sensors may be utilized and may be positioned in various positions to sense the portions of the received air stream AS. Conversely, in an alternative embodiment, air stream sensors may be positioned to sense the portion of the air stream that is received at the inlet aperture 619, rather than sense the air stream received away from the inlet aperture 619.

In one embodiment, the portion of the air stream AS received at the inlet aperture 19 is maximized by adjusting both the air stream velocity and the angle of the discharge nozzle 18. FIGS. 25A-25D show an embodiment in which the discharge nozzle 18 may be positioned at one of two discrete positions, angles A°, B°. In these examples, the dashed lines for the air streams AS1 and AS3 represent relatively low velocity air streams and the air streams AS2 and AS4 represent relatively high velocity air streams. To maximize the portion of the air stream received at the inlet aperture 19, the air discharge nozzle 18 is moved to a one of the angles A°, B°. The velocity of the air stream is adjusted to maximize the portion of the air stream received at the inlet aperture 19. Different operating conditions may permit lesser air stream velocities or lesser discharge angles, or both. FIG. 25A shows an example in which the air stream AS1 is discharged at a relatively straight angle A and at a relatively low velocity. FIG. 25B shows an example in which the air stream AS2 is discharged at the same angle A° as shown in FIG. 25A, but at a higher velocity. If the same velocity was used as in the air stream AS1 shown in FIG. 25A, a greater portion of that air stream AS1 would miss the inlet aperture 19, as shown in FIG. 25B. FIG. 25C shows an example in which a relatively low velocity air stream AS3 is discharged at a steeper angle B°.

FIG. 25D shows an example in which a higher velocity air stream AS4 is discharged from this same steeper angle B that is used in FIG. 25C. As with the example of FIG. 25B, the operating conditions represented in FIG. 25D would cause a larger portion of a lower velocity air stream, such as AS3, to miss the inlet aperture 19. By adjusting both the angle of the discharged air stream and the velocity of the air stream, the air curtain arrangement may operate more efficiently in certain environments.

Although the present invention has been described with respect to particular embodiments thereof, variations are possible. The present invention may be embodied in specific forms without departing from the essential spirit or attributes thereof. In addition, although aspects of an implementation are described as being stored in memory, one skilled in the art will appreciate that these aspects can also be stored on or read from other types of computer program products or computer-readable media, such as secondary storage devices, including hard disks, floppy disks, or CD-ROM; other forms of RAM or read-only memory (ROM); or any other type of storage arrangement. Also, examples of psychrometric charts are illustrated in standard convention with dry bulb temperature on the horizontal axis, increasing left to right, and humidity on the vertical axis increasing bottom to top. Accordingly, a point to the right of a line on this plot has a higher temperature than the line itself, at the same humidity. In other embodiments, the psychrometric chart could be prepared with a different convention. It is desired that the embodiments described herein be considered in all respects, illustrative and not restrictive and that reference be made to the appended claims and their equivalents for determining the scope of the invention.

What is claimed is:

1. An air curtain arrangement comprising:
    an air curtain unit, comprising
        a discharge nozzle that discharges an air stream across a doorway having a relatively cold side and a relatively warm side;
        a return air duct having an inlet aperture that receives at least a portion of the air discharged across the opening; and
        a controller that controls a direction of the air stream discharged by the discharge nozzle, based upon a difference between (1) a temperature of the air received at the return air plenum, and (2) an average of temperatures on opposing sides of the air curtain unit.

2. The air curtain arrangement of claim 1, wherein the controller controls an actuator that positions the discharge nozzle.

3. The air curtain arrangement of claim 2, wherein the discharge nozzle comprises first and second spaced-apart blades that direct the flow of air therebetween, and wherein the actuator connects to at least one of the blades to adjust the direction of the air discharged by the discharge nozzle.

4. The air curtain arrangement of claim 1, further comprising a plenum temperature sensor positioned proximate the return air duct that senses a plenum temperature of the air received at the inlet aperture and communicates the plenum temperature to the controller.

5. The air curtain arrangement of claim 4, wherein the plenum temperature sensor is positioned within the air return duct, proximate the inlet aperture.

6. The air curtain arrangement of claim 1, further comprising first and second plenum temperature sensors that measure plenum temperatures of the air received at the return air duct at first and second points, respectively, and communicate the first and second plenum temperatures to the controller, wherein the controller controls the direction of the air stream by independently controlling first and second directions of the air stream at first and second points, respectively, wherein the controller controls the first direction of the air stream at the first point, based upon (1) the first plenum temperature, and (2) an average of temperatures on opposing sides of the air curtain unit; and wherein the controller controls the second direction of the air stream at the second point, based upon (1) the second plenum temperature, and (2) the average of temperatures on opposing sides of the air curtain unit.

7. The air curtain arrangement of claim 1, further comprising one or more temperature sensors that sense temperatures on opposing sides of the air curtain arrangement and communicate the sensed temperatures to the controller.

8. The air curtain arrangement of claim 7, wherein the controller controls the direction of the air stream by comparing the temperature of the air received at the return air plenum to the average of the temperatures on the opposing sides of the air curtain arrangement.

9. The air curtain arrangement of claim 7, wherein the controller controls the direction of the air stream to minimize the difference between (1) the return air plenum temperature and (2) the average of the temperatures on opposing sides of the air curtain arrangement.

10. The air curtain arrangement of claim 7, wherein the temperature sensors continuously send temperature data to the controller, and wherein the controller controls the direction of discharged air dynamically, to adjust the direction of air stream discharge as the temperature data changes.

11. The air curtain arrangement of claim 1, wherein the air curtain arrangement comprises a plurality of air curtain units, each having a discharge nozzle and a return air plenum, and wherein the discharge nozzles are controlled independent of each other based upon (1) the average of temperatures on opposing sides of each respective air curtain unit and (2) a plenum temperature of each respective air curtain unit.

12. The air curtain arrangement of claim 11, wherein the controller controls an upper and a lower air discharge direction for each of the plurality of air curtain units based upon an upper and lower plenum temperature for each of the plurality of air curtain units.

13. An air curtain arrangement comprising:
an air discharge means that discharges an air stream across a doorway having a relatively cold side and a relatively warm side;
an air return means that receives a portion of the discharged air and returns the air to the air discharge means; and
a controller that controls direction of the air discharge means to maximize the portion of discharged air that is received at the air return means, wherein the controller controls the direction of the discharged air based upon a difference between (1) a temperature of the discharged air received at the air return means, and (2) an average of a temperature of the cold side and a temperature of the warm side.

14. The air curtain arrangement of claim 13,
further comprising at least one air stream sensor positioned adjacent to the air return means, which senses a portion of the air stream that is received by the air return means, and
wherein the controller controls the direction of the discharged air based upon the portion of the air stream sensed by the at least one air stream sensor.

15. The air curtain arrangement of claim 13, wherein the controller controls the velocity of the air stream to maximize the portion of the discharged air that is received at the air return means.

16. The air curtain arrangement of claim 15, wherein the controller causes the air discharge means to discharge the air stream at one of a plurality of pre-determined directions.

17. An air curtain arrangement for a cold storage doorway, comprising:
means for directing an air stream across the doorway having a relatively warm side and a relatively cold side;
means for receiving at least a portion of the air stream;
means for maintaining a temperature of the air stream based on a humidity ratio associated with the doorway; and
means for controlling a discharge direction of the air stream in order to maximize the portion of the air stream that is received by the means for receiving, wherein the means for controlling a discharge direction controls the direction of the air stream by comparing a temperature of the portion of the air stream that is received by the means for receiving to an average of temperatures on opposing sides of the doorway.

\* \* \* \* \*